US011510825B2

(12) United States Patent
Arizti

(10) Patent No.: US 11,510,825 B2
(45) Date of Patent: Nov. 29, 2022

(54) ABSORBENT ARTICLE SENSOR ACTIVATION

(71) Applicant: The Procter & Gamble Company, Cincinnati, OH (US)

(72) Inventor: Blanca Arizti, Brooklyn, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 321 days.

(21) Appl. No.: 16/905,076

(22) Filed: Jun. 18, 2020

(65) Prior Publication Data

US 2021/0393447 A1 Dec. 23, 2021

(51) Int. Cl.
*A61F 13/42* (2006.01)
*G01N 21/25* (2006.01)
*G01N 21/80* (2006.01)
*A61F 13/551* (2006.01)

(52) U.S. Cl.
CPC ........ *A61F 13/42* (2013.01); *A61F 13/55105* (2013.01); *G01N 21/251* (2013.01); *G01N 21/80* (2013.01); *A61F 2013/422* (2013.01); *A61F 2013/427* (2013.01); *A61F 2013/429* (2013.01)

(58) Field of Classification Search
CPC ............... A61F 13/42; A61F 13/55105; A61F 2013/422; A61F 2013/427; A61F 2013/429; G01N 21/251; G01N 21/80
See application file for complete search history.

(56) References Cited

U.S. PATENT DOCUMENTS

| 8,940,959 | B2 | 1/2015 | Liu |
| 9,726,763 | B2 | 8/2017 | Dempsey et al. |
| 9,907,707 | B2 | 3/2018 | Lavon |
| 9,913,608 | B2 | 3/2018 | Lewis et al. |
| 10,159,607 | B2 | 12/2018 | Monson et al. |
| 10,264,250 | B2 * | 4/2019 | Maltz ................. G06Q 30/0207 |
| 10,271,998 | B2 | 4/2019 | Lavon |

(Continued)

FOREIGN PATENT DOCUMENTS

| CN | 111107784 A * | 5/2020 | ............. A61B 5/002 |
| EP | 3184039 A1 | 6/2017 | |

(Continued)

OTHER PUBLICATIONS

All Office Actions, U.S. Appl. No. 17/346,313.

(Continued)

*Primary Examiner* — Chico A Foxx
(74) *Attorney, Agent, or Firm* — Steven Robert Chuey

(57) ABSTRACT

The present disclosure is directed to techniques for coupling activation of sensor devices with use of authorized products. A system includes a sensor device. The sensor device includes a housing that attaches to an absorbent article configured to absorb and contain bodily exudates. The sensor device further includes at least one sensor formed on or within the housing configured to capture sensor data in association with wear of the absorbent article. The system also includes a processor that executes computer executable components. The computer executable components include a communication component that receives an activation code and an activation component that activates a functionality based on the receipt of the activation code.

21 Claims, 18 Drawing Sheets

(56) References Cited

U.S. PATENT DOCUMENTS

| | | | |
|---|---|---|---|
| 10,285,871 B2 | 5/2019 | Arizti | |
| 10,292,112 B2 | 5/2019 | Lavon | |
| 10,624,795 B2 | 4/2020 | Christiansen et al. | |
| 2003/0206109 A1* | 11/2003 | Yang | A61F 13/42 340/573.5 |
| 2005/0124947 A1 | 6/2005 | Fernfors | |
| 2006/0238360 A1 | 10/2006 | Ho | |
| 2008/0094226 A1* | 4/2008 | O'Shea | A61B 5/6804 340/572.1 |
| 2008/0278336 A1 | 11/2008 | Ortega et al. | |
| 2012/0116337 A1* | 5/2012 | Ales | G01N 21/645 604/361 |
| 2012/0173249 A1* | 7/2012 | Popp | A61F 13/51498 235/487 |
| 2013/0076509 A1* | 3/2013 | Ahn | A61F 13/42 340/539.12 |
| 2014/0155850 A1* | 6/2014 | Shah | A61F 13/42 604/361 |
| 2014/0379285 A1 | 12/2014 | Dempsey et al. | |
| 2016/0029957 A1* | 2/2016 | Faybishenko | A61B 5/150022 600/309 |
| 2016/0307430 A1* | 10/2016 | Chen | G08B 21/20 |
| 2017/0150917 A1* | 6/2017 | Brief | A61B 5/0022 |
| 2017/0252225 A1 | 9/2017 | Arizti et al. | |
| 2017/0252226 A1 | 9/2017 | Arizti | |
| 2017/0351271 A1 | 12/2017 | Hasenoehrl | |
| 2017/0353323 A1 | 12/2017 | Apte | |
| 2018/0167499 A1* | 6/2018 | Torvinen | A61B 5/6804 |
| 2018/0271722 A1* | 9/2018 | Gonzalez Martinez | A61F 13/5511 |
| 2019/0087885 A1* | 3/2019 | Wen | G06Q 30/0633 |
| 2019/0167489 A1 | 6/2019 | Hellmold et al. | |
| 2019/0180341 A1* | 6/2019 | Matra | G06Q 30/0633 |
| 2019/0336343 A1 | 11/2019 | Etchells et al. | |
| 2020/0060886 A1 | 2/2020 | Arizti et al. | |
| 2020/0085990 A1 | 3/2020 | Gao et al. | |
| 2020/0088701 A1 | 3/2020 | Jung et al. | |

FOREIGN PATENT DOCUMENTS

| | | |
|---|---|---|
| EP | 3332698 A1 | 6/2018 |
| WO | 2018229017 A1 | 12/2018 |
| WO | WO-2021198451 A * | 10/2021 |

OTHER PUBLICATIONS

All Office Actions, U.S. Appl. No. 16/904,949.
All Office Actions, U.S. Appl. No. 16/904,936.
Unpublished U.S. Appl. No. 16/904,936, filed Jun. 18, 2020, to first inventor et al.
Unpublished U.S. Appl. No. 16/904,949, filed Jun. 18, 2020, to first inventor et al.
Unpublished U.S. Appl. No. 17/346,313, filed Jun. 14, 2021, to first inventor et al.
PCT Search Report and Written Opinion for PCT/US2021/037979 dated Oct. 6, 2021, 12 pages.

* cited by examiner

ABSORBENT ARTICLE SENSOR ACTIVATION

TECHNICAL FIELD

This application relates to absorbent article sensor systems and more particularly to techniques for coupling activation of absorbent article sensor devices with use of authorized products.

BACKGROUND

Absorbent articles for personal hygiene, such as disposable diapers for infants, training pants for toddlers or adult incontinence undergarments are designed to absorb and contain bodily exudates, in particular, large quantities of urine. These absorbent articles comprise several layers providing different functions, for example a topsheet, a backsheet and in-between an absorbent core, among other layers. The function of the absorbent core is to absorb and retain the exudates for a prolonged amount of time, for example overnight for a diaper, minimize re-wet to keep the wearer dry and avoid soiling of clothes or bed sheets.

It has been proposed to incorporate sensors into absorbent articles to facilitate sensing usage information (e.g., timing of initiation and level of saturation associated with urination and/or defecation) and/or providing notifications to users (e.g., caregivers, article manufacturers, etc.) regarding the usage information. However, it is believed that improvements are still necessary for such sensors systems.

Counterfeiting of products is an ever-growing problem in numerous industries. Indeed, counterfeiting of absorbent article sensor products is foreseeable as competitors in the industry may attempt to develop and sell off-brand or counterfeited products for lower costs. Consequently, manufacturers desire mechanisms to mitigate use of proprietary sensor devices with absorbent articles produced by other manufactures that have not been safely cleared for use and/or validated for proper performance with the devices. Further, manufacturers desire mechanisms to ensure and track authorized use of their products for providing loyal customers with ancillary services.

SUMMARY

The invention comprises the features of the independent claims herein. A system comprises a sensor device. The sensor device comprises a housing that attaches to an absorbent article configured to absorb and contain bodily exudates. The sensor device also comprises at least one sensor formed on or within the housing configured to capture sensor data in association with wear of the absorbent article. The system comprises a processor that executes computer executable components. The computer executable components comprise a communication component that receives an activation code and an activation component that activates a functionality based on the receipt of the activation code.

Additionally, a system is provided that comprises a sensor device configured to removably attach to absorbent articles and generate sensor data in association with wear of the absorbent articles; and a processor that executes the computer executable components. The computer executable components comprise a code capture component that captures a code associated with a sensor device, and a validation component that performs a code validation process to determine whether the code is valid. The computer executable component further comprises an activation component that activates a functionality based on a determination that the code is valid.

A method comprises receiving, by a sensor device comprising or operatively coupled to a processor, an activation code from a device external to the sensor device, wherein the sensor device removably attaches to an absorbent article configured to absorb and contain bodily exudates. The method further includes activating, by the sensor device, a functionality of the sensor device based on receipt of the activation code.

In various embodiment, the functionality comprises operation of one of the group consisting of: one or more sensors of the sensor device, the processor, storing logic that provides for storing captured and/or processed sensor data in a memory, a communication protocol that provides for transmitting the captured and/or processed sensor data to an external user device, a software application, one or more computer executable components, a restriction protocol to restrict any of the foregoing functionalities to use of the sensor device with one or more absorbent articles made by a same manufacturer of the absorbent article and combinations thereof.

Elements described in the disclosed systems can be embodied in different forms such as a computer-implemented method, a computer program product, or another form.

DETAILED DESCRIPTION

Figure 1:
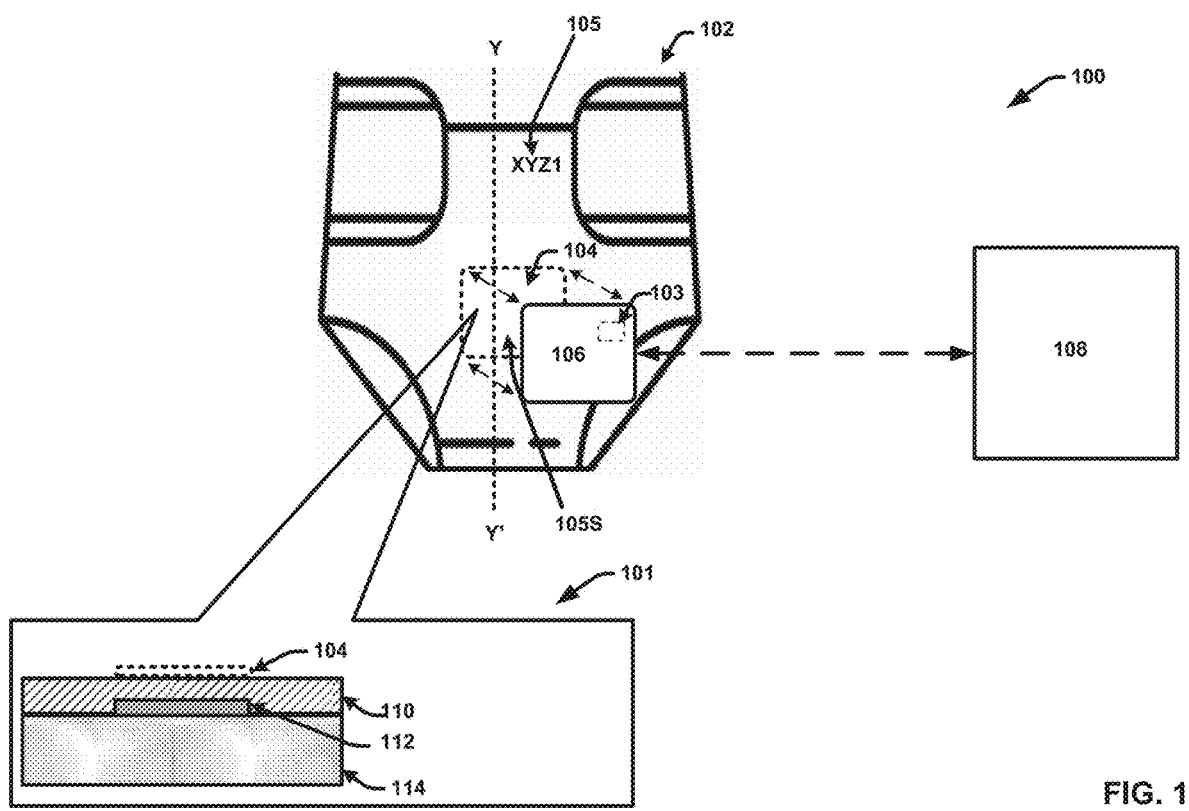
FIG. 1 illustrates a block diagram of an example, non-limiting system for coupling activation of an absorbent article sensor device with use of authorized products in accordance with one or more embodiments of the disclosed subject matter.

The following detailed description is merely illustrative and is not intended to limit embodiments and/or application or uses of embodiments.

"Absorbent article" as used herein refers to a variety of devices which are placed or worn against or in proximity to the body of the wearer to absorb and contain various exudates discharged from the body, such as disposable diapers. Typically, these absorbent articles comprise a topsheet, a backsheet, an absorbent core and optionally an acquisition system (which may be comprised of one or several layers) and other components, with the absorbent core normally placed between the backsheet and the acquisition system or topsheet. The function of the absorbent core is to absorb and retain the exudates. Although various embodiments of the disclosed subject matter are exemplified in association with the absorbent article being a disposable diaper, it should be appreciated that the disclosed techniques can be applied to a variety of other types of absorbent articles, including reusable diapers (e.g., cloth diapers), absorbent inserts which may be disposable or reusable and may be used in combination with reusable outer covers, pants, training pants, pads, adult incontinence products, and/or feminine hygiene products (including, for example, sanitary napkins and tampons).

"Sensor device" refers to any electrical device that can be attached to and/or integrated on or within an absorbent article that provides for capturing and/or generating sensory feedback data associated with wear of the absorbent article via one or more sensors formed on or within the sensor device. In various embodiments, the sensor device can be configured to removably attach to disposable diapers and/or other absorbent articles.

"Sensory feedback data" (or simply "sensory feedback") as used herein refers to any type of data captured by one or more sensors formed on or within the sensor device and/or determined or inferred based on the captured sensor data. In this regard, unless context warrants particular distinctions among the terms, sensory feedback data can include raw sensor measurements (e.g., raw color sensor data, raw motion sensor measurements, etc.) and/or processed feedback information determined based on the raw sensor measurements using one or more algorithms, heuristics, machine learning models, etc. (e.g., a determined saturation/wetness level, a determined activity level, etc.). Sensory feedback data includes usage data and/or activity data.

"Usage" in relation to information captured, to be captured, inferred/determined from information captured, processed, detected, stored and/or transmitted, or otherwise used in the sensor systems described herein refers information regarding occurrence and/or timing of the exudation events (e.g., urination, defecation), amount of bodily exudates (e.g., by volume, by weight) associated with an exudation event, saturation levels, time to saturation of the absorbent article, loading status, amount of bodily exudates contained within the absorbent article over a period of time, frequency of exudation events, frequency of article changes, duration of exposure time to bodily exudates, type of the bodily exudates (e.g., urine, feces, discharge, etc.), characteristics of the bodily exudates (e.g., runny bowel, mushy/pasty bowels, viscosity of exudates, coloration of the exudates, etc.), biomarkers present in the bodily exudates, and/or other details related to the use of an absorbent article.

"Activity" in relation to information captured, to be captured, inferred/determined from information captured, processed, detected, stored and/or transmitted, or otherwise used in the sensor systems described herein refers to information regarding exertion levels, movement, exertion and/or movement patterns, sleep/wake patterns, positions, motions, defined movements and motions (e.g., laying, laying on back, laying on stomach, sitting, kicking, walking, crawling, grabbing/pulling on diaper, etc.), and/or other details related to the actions of the wearer during wear of an absorbent article.

"Joined" or "attached" as used herein encompasses configurations whereby an element is directly secured to another element by affixing the element directly to the other element, and configurations whereby an element is indirectly secured to another element by affixing the element to intermediate member(s) which in turn are affixed to the other element. The terms further include embodiments in which a pocket or other connector is formed in or attached to an area of the absorbent article. Further, these terms include configurations in which the elements are removably or non-removably attached.

"Processor" as used herein refers to a device that executes machine/computer executable instructions or components stored in memory. A processor as used herein includes, but is not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize use of space or enhance performance of user equipment. A processor can also be implemented as a combination of computing processing units.

"Component as it relates to a sensor device, a system incorporating a sensor device and/or other machinery herein refers to a computer-related entity or an entity related to an operational machine with one or more specific functionalities. The entities may be hardware, software, a combination of hardware and software, or software in execution. One or more components can reside within a process and/or thread of execution and a component can be localized on one computer and/or distributed between two or more computers. Components can communicate via local and/or remote processes. A component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

"Memory" as used herein refers to mechanism(s) used to retain information, such as executable instructions or components. As used herein, terms such as "store," "storage," "data storage," "database," and substantially any other information storage element relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. Additionally, the disclosed memory components of systems or computer-implemented methods herein are intended to include, without being limited to including, these and any other suitable types of memory.

FIG. 1 illustrates a block diagram of an example, non-limiting system 100 for coupling activation of sensor devices with use of authorized products. Embodiments of systems described herein can include one or more machine-executable components embodied within one or more machines (e.g., embodied in one or more computer-readable storage media associated with one or more machines). Such components, when executed by one or more machines (e.g., processors, computers, computing devices, virtual machines, etc.), can cause the one or more machines to perform the operations described.

System 100 includes an absorbent article 102 (in the form of a diaper), a sensor device 106 and an external user device 108. One or more functionalities of the system 100 can require activation based on receipt and/or validation of an activation code 105, wherein the activation code is received and/or otherwise made accessible to the user based on purchase and/or use of diapers (and/or other products) from an authorized entity/manufacturer. In some embodiments, the article may also comprise a secret code 105S, which is not visible as a code to the user. The secret code may be detectable by one or more sensors and/or by an external user device 108. As discussed in more detail with respect to FIG. 9, the system may validate the activation code based on a combination of the activation code and the secret code.

In one or more embodiments, the sensor device 106 can be configured to removably attach to the absorbent article 102 and capture and/or generate sensory feedback data associated with wear of the absorbent article 102 using one or more sensors 103 formed on or within a housing (described infra) of the sensor device 106. Although system 100 depicts a single absorbent article 102 for use with the sensor device 106, the sensor device 106 can be designed to be reused with and reattached to a plurality of absorbent articles (e.g., disposable diapers). In various embodiments, the sensor device 106 can be configured to removably attach to the absorbent article 102 at or near an attachment zone 104 marked on exterior portion of the absorbent article 102. The location of the attachment zone 104 can vary depending on the type of the absorbent article 102, the type of sensory feedback data the sensor device 106 is configured to capture/detect, and/or the mechanism via which the sensor device 106 captures/detects the sensory feedback data in association with attachment to the absorbent article 102.

In some implementations, the sensory feedback data can include information regarding one or more biomarkers present in the bodily exudates. In various implementations, the sensor device 106 can capture and/or detect information based on responses/reactions reflected in one or more indicators 112. With these implementations, the absorbent article 102 can comprise one or more indicators 112 formed on or within the absorbent article 102 that generate a response/reaction to indicate certain information (e.g., the presence and/or absence of bodily exudates), and the sensor device 106 can include one or more sensors configured to detect the response/reaction.

For example, call out box 101 presents an enlarged view of a transversal cross-section of a portion of the absorbent article 102 located directly below the attachment zone 104 in accordance with some example embodiments. As shown in call out box 101, the absorbent article 102 comprises a backsheet 110 as an outer layer of the absorbent article 102. The absorbent article 102 further includes one or more internal layers 114 formed on or joined to the backsheet 110. Such internal layers 114 may include one or more layers of an acquisition system, one or more layers of an absorbent core, and/or one or more inner layers of the backsheet. The absorbent article 102 can further include one or more indicators 112 formed between the backsheet 110 and at least one of the internal layers 114 within a region of the absorbent article that at least partially overlaps the attachment zone 104. For example, in some embodiments, the housing (discussed infra with reference to FIGS. 2A and 2B) of the sensor device 106 can be adapted to be physically coupled to the absorbent article 102 such that the sensor device 106 is further communicatively coupled to the one or more indicators 112.

In some embodiments, at least one indicator 112 may react to usage and/or activity information (or other conditions to be monitored) via one or more changes in a property of the indicator (e.g., a physical, chemical and/or biological property such as color, smell, sound, pH, or the like). By way of nonlimiting example, at least one indicator 112 may react to the presence and/or absence of bodily exudates and/or one or more properties of those bodily exudates as absorbed within the absorbent article. The property or state of the indicator 112, in turn, can be detected by one or more sensors formed on or within a housing of the sensor device 106 when the sensor device 106 is physically and/or communicatively coupled to the absorbent article 102 (e.g., at or near the attachment zone 104). In one particular implementation, the at least one indicator 112 can comprise an optical property changing composition or device (e.g., a color-changing composition or device, such as a color changing indicator) that changes an optical property based on the presence and/or absence of bodily exudates within the one or more internal layers 114 of the absorbent article 102. A color changing indicator can change its color, for example, based on the presence and/or absence of bodily exudates and/or in response to some other condition being monitored with respect to the absorbent article 102.

Essentially any known color-changing indicator that responds to the absence or presence of bodily exudates or other conditions to be monitored with respect to the absorbent article 102 can be used. In some implementations, the absorbent article 102 can employ a color-changing indicator, such as a color strip, which comprises a chemical substance that can induce a color change in the color strip when bodily exudates are present within the one or more internal layers 114. One useful form of a color-changing indicator comprises a pH-sensitive indicator. With these embodiments, the sensor device 106 can include one or more optical sensors, such as a color sensor (also referred to as a colorimeter), to detect information based on detection of a defined color change in the color indicator. For example, the color sensor can provide an output that varies depending on usage information (e.g., the presence or absence of bodily exudates, an amount of the bodily exudates), which is identified/detected by an optical property (e.g., a color) in the color indicator that is observed by the sensor.

Figure 2A:
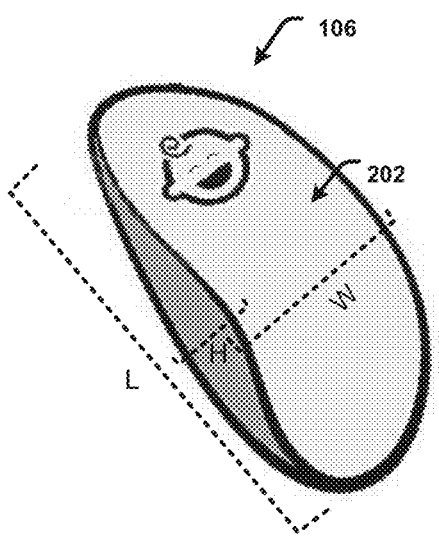
FIGS. 2A and 2B present a schematic illustration of an example sensor device in accordance with one or more embodiments of the disclosed subject matter.
Figure 2B:
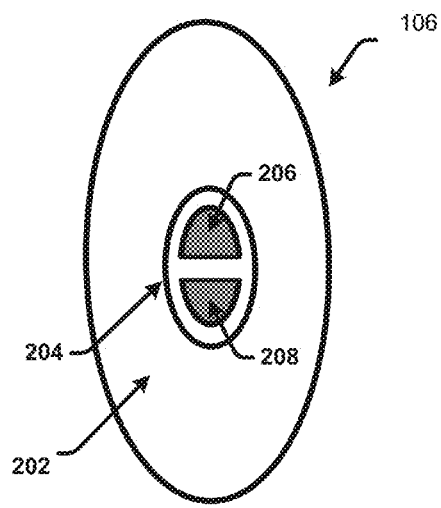

In this regard, FIGS. 2A and 2B present a schematic illustration of an exemplary sensor device 106. FIG. 2A presents a three-dimensional view of top and side surfaces of the housing 202. FIG. 2B presents a two-dimensional view the backside of the sensor device 106, wherein the backside of the sensor device opposes the topside of the housing that includes the baby image/symbol as shown in FIG. 2A, and wherein the backside of the housing 202 is adapted to be attached to and face the attachment zone 104 of the absorbent article.

With reference to FIGS. 2A and 2B in view of FIG. 1, in various embodiments, the housing 202 and/or the absorbent article 102 can include one or more connectors (not shown) for removably attaching the sensor device 106 to the absorbent article 102. The connectors can be provided such that the sensor device 106 can be attached to and detached from the absorbent article 102. In one non-limiting example, the sensor device 106 can be attached and detached to an area of the absorbent article at least partially overlapping an indicator 112.

For example, in various embodiments, the housing 202 and/or the absorbent article 102 can employ various connectors which allow for detachment and can also allow for refastening of the sensor device 106 to the absorbent article 102 at or near the attachment zone 104. In some implementations, the connectors can include one or more adhesives or cohesives formed on the attachment zone 104 and/or on the backside of the housing 202. Such connectors can further include one or more mechanical fasteners, including strap-based fasteners, hook-and-loop-fasteners (e.g., Velcro™), or fasteners comprising at least one button or at least one magnet. In another implementation, a pocket can be formed at or near the attachment zone 104 of the absorbent article 102 and the sensor device 106 can be inserted into the pocket. For example, some absorbent articles can be provided as pants comprising a crotch portion and a belt portion. The crotch portion and the belt portion can be joined adhesively or mechanically. In the area of adhesive joining, a certain portion can be free of adhesive and accessible from the outside. This portion can then serve as a pocket for receiving the sensor device 106. A belt, strap or other device may be used to place and hold the sensor device 106 relative to the absorbent article 102. The sensor device 106 can similarly be joined or held to an article of clothing worn by the wearer of the absorbent article.

The sensor device 106 includes a detection unit 204 configured to detect configured sensory feedback data from one or more sensors 206. In the embodiment shown in FIG. 2B, the detection unit 204 includes an optical sensor 206 and is configured to detect optical property changes reflected in the one or more indicators 112 when the sensor device is attached to the absorbent article at or near the attachment zone. The optical sensor 206 and a light source 208 (e.g., an LED) may be located on the backside of the sensor device 106. In accordance with this non-limiting example, the backsheet 110 of the absorbent article can comprise a transparent or semitransparent material that allows the detection unit 204 to view the optical property changes in the indicator 112 through the backsheet 110. Additionally, or alternatively, one or more indicators 112 can be exposed on or within a region of the backsheet 110 located directly in the attachment zone 104. The backside of the housing 202 can also include a transparent window (e.g., glass, plastic, or another suitable transparent material) or opening through which the optical sensor 206 and the light source 208 are exposed to the environment. In some implementations, the window/opening and/or the optical sensor 206 and light source 208 can further be can be hermetically sealed within the housing 202.

In one or more embodiments, the optical sensor 206 can be configured to measure one or more light levels of a color strip indicator disposed within the absorbent article. In non-limiting examples, the optical sensor 206 can measure four light levels—clear, red, green and blue—with a sixteen (16) bit resolution. The clear level can correspond to a measure of an overall light intensity and the red, green and blue levels can correspond to intensity in the relevant parts of the spectrum from the color strip indicator. In this embodiment, the sensor device can take multiple measurements with the optical sensor 206. For example, in a first operation, the optical sensor 206 can be read without the light source 208 illuminated to determine a background light level. Another reading of the optical sensor 206 can also be taken in another operation with the light source 208 illuminating the color change indicator to measure the clear, red, green and blue (RGB) light levels. A difference between the two measurements is obtained in a third operation and represents a color of the color strip indicator. The clear color level can be used to normalize the RGB values. Saturation levels corresponding to one or more intermediate states of the color strip indicator can also be determined, such as from the hue, saturation and brightness (HSB) values in combination with or instead of the RGB values.

The optical sensor 206 can be spaced from the light source 208 so that direct light from the light source 208 is reduced or eliminated at the optical sensor 206. Similarly, too large a spacing between the optical sensor 206 and the light source 208 can reduce the signal strength at the optical sensor 206. The optical sensor 206 can be spaced at least about 5.0 millimeters (mm), or at least about 8.0 mm, or at least about 10.0 mm, or from about 5.0 to about 20.0 mm, or from about 10.0 to about 15 mm from the light source 208, reciting for each range every 1 mm increment therein.

In addition to spacing between the optical sensor 206 and the light source 208, other factors may also affect light level measurements of the optical sensor 206. For example, temperature, location of the sensor device 106 on the article, the type, material and color of a connector (e.g., adhesive, tape, hook and loop, strap and other materials) disposed between the sensor device and the indicator, orientation of the sensor device 106 relative to the indicator, orientation of transmit and receive windows of the sensor device 106 and the article, force of application of the sensor device 106 against the article, ambient light, position of an attachment zone 104 on the article and position of the sensor device 106 relative to the indicators 112 within the article (e.g., in a cross-direction) such that the optical sensor 206 detects other portions of the article disposed near the one or more indicators 112.

The size, shape, and/or dimensions of the housing 202 can vary. In some implementations in which the sensor device 106 is designed to be removably attached to disposable diapers, for safety (so as to not become a choking hazard) and convenient handling, the housing 202 can have a length (L) of at least 1.0 centimeters (cm), 2.0 cm, 3.0 cm, 4.0 cm or more (but normally less than 15.0 cm), a width (W) of least 1.0 cm, 2.0 cm, 3.0 cm or more (but normally less than 15.0 cm), and a height (H) of at least 0.5 centimeters, 1.0 cm, 2.0 cm, 3.0 cm, 4.0 cm or more (but normally less than 15.0 cm).

The material employed for the housing 202 can also vary. In some implementations, the housing 202 can be formed with a rigid material (e.g., a rigid plastic). In other implementations, the housing 202 can be formed with a flexible or partially flexible material. To be flexible, the sensor device 106 can incorporate flexible electronic components (and boards). Some suitable materials for the housing 202 can include but are not limited to, silicon, plastic, a thermoplastic, a thermoplastic elastomer (TPE), a confection, a thermosetting polymer, rubber, and the like.

With reference again to FIG. 1, although a pH sensitive color strip indicator is discussed with respect to various example embodiments, indicators 112 are not limited thereto. Rather, indicators 112 can include any indicator that changes color, or another physical property, directly or indirectly related to usage of the article and/or wearer activity. For example, color change materials that change from no color to one or more colors, from one or more colors to no colors, change colors in other color ranges than the pH sensitive adhesive described herein, materials that change color or appearance based on factors other than pH changes, such as but not limited to, temperature, wetness, odor, enzymes, organic components, inorganic components (e.g., salt level), colored SAP/AGM, mechanical forces (e.g., strain, stretch) or the like.

Indicators 112 can also comprise biological or physical sensor materials. For example, physical sensors can be provided by a material, which changes its color when the material is stretched. Stretching of a material can be induced by the swelling of the absorbent core, or other portions, of the absorbent article 102. Biological sensors can include a bioreceptor that interacts with an analyte of interest, such as trypsin or urease. A bioreceptor, for example, can use reagent/analyte interactions that provide a property change (e.g., a color or other optical change) in the absorbent article 102 upon detection of a particular analyte of interest (e.g., a biomarker). Additionally, or alternatively, a bioreceptor can use an immobilized binding reagent capable of binding to an analyte of interest. The immobilized reagent can be disposed on or within one or more layers of the absorbent article 102 adjacent to the attachment zone.

Additionally, or alternatively, indicators 112 can comprise a material selected from the group comprising, consisting essentially of or consisting of: thermochromic inks, thermochromic dyes, thermochromic liquid crystalline materials, and combinations thereof. These indicators can, for example, serve to monitor other conditions associated with the absorbent article and/or wearer, such as body temperature or fever indication.

The sensor device 106 can include various other types of sensors that can capture and/or generate sensory feedback data regarding usage of the absorbent article and/or activity of the wearer. The sensor device 106 can include one or more motion sensors (e.g., an accelerometer, a gyroscope, etc.), image sensors, biosensors, biochemical sensors, temperature sensors, force/pressure sensors, humidity sensors, acoustic sensors, an RFID reader/sensor, biofeedback sensors configured to detect physiological parameters associated with the wearer (e.g., heart rate, temperature, and other vital signs, biomarkers present in bodily exudates and the like), and the like. Additionally, or alternatively, at least one sensor can be configured to sense, detect or otherwise capture sensor data reflective on a behavior of the wearer, pressure and irritation associated with fit and/or wear of the absorbent article, and the like. Further, the activity information can include motion and/or movement data (e.g., captured via one or more motion sensors) that can be correlated to defined bodily movements and/or positions, movement patterns, activity patterns (e.g., sleep/wake patterns), activity levels, and the like.

In addition to the one or more sensors, the sensor device 106 can further include suitable electronic circuitry (e.g., hardware), software, or a combination thereof, that provides for processing of raw sensor measurements representative of a measured property (e.g., a wetness/saturation level, an amount of bodily exudates, an activity level, an activity pattern, a defined movement or motion, etc.) as captured via the one or more sensors of the sensor device 106 into a digital signal corresponding to the measured property. For example, such electronic circuitry can include but is not limited to, excitation control elements, amplification elements, analogue filtering elements, data conversion elements, compensation elements, and the like. As described in greater detail infra with reference to FIG. 9, the sensor device 106 can also include or be operatively coupled to at least one memory that stores computer executable instructions and at least one processor (e.g., a microprocessor) that executes the computer executable instructions stored in the memory.

The sensor device 106 can also include suitable communication hardware and/or software that provides for wireless (and/or wired) communication between the sensor device 106 and the least one external user device 108. The external user device 108 can include essentially any type of computing device capable of at least receiving information from the sensor device 106. For example, the external user device 108 can include but is not limited to: a mobile phone, a smartphone, a smartwatch, a tablet personal computer, a laptop computer, a desktop computer, a video monitoring device (e.g., a video baby monitor device), an audio monitoring device (e.g., an audio baby monitor device), an augmented reality (AR) device, a virtual reality (VR), a heads-up display (HUD), a smart speaker device, another sensor device, an IoT device, a television, an Internet enabled television, and similar types of devices.

For example, in some embodiments, the sensor device 106 can be configured to transmit captured sensor data to an external user device 108 associated with a caregiver and/or the wearer (or another suitable entity) for processing and/or presentation to the caregiver etc. via a display, speaker, or another suitable output device of the external user device 108. The external user device 108 can be configured to process and/or analyze the sensor data to determine and/or infer sensory feedback data based on captured sensor measurements. For example, the external user device 108 can receive sensor data from the sensor device 106 identifying or indicating a measured property and/or status of at least one indicator 112. In another example, the external user device 108 can receive sensor data including chemical sensor measurements, temperature sensor measurements, motion sensor measurements, pressure sensor measurements, and the like, as captured via corresponding sensors located on or within the sensor device 106. The external user device 108 can further process/analyze the received sensor data using predefined processing logic (e.g., algorithms, heuristics, machine learning models, defined correlations, tracked data correlations, etc.) to determine and/or infer sensory feedback data regarding usage and/or activity. In some embodiments, the external user device 108 can further present or otherwise render the sensory feedback information at the external user device 108. For example, in implementations in which the absorbent article 102 is a diaper, based on a determination that the sensor data indicates the diaper is wet, the external user device 108 can generate and render a notification at the external user device notifying the caregiver that the diaper needs changing. In addition to processing and/or rendering the captured sensor data to provide feedback to the user, the sensor device 106 and/or the external user device 108 can also store the sensor data and/or the sensory feedback data determined therefrom in suitable data storage for data aggregation.

Additionally, or alternatively, the sensor device 106 itself can include onboard processing logic for processing the sensor data to determine and/or infer sensory feedback data based on the captured sensor data measurements. With these embodiments, the sensor device 106 can be configured to transmit the processed sensory feedback data to the external user device 108 for presentation to the device user and/or for further analytical processing (e.g., by the external user device 108, an application server for the connected care system, another system or the like). For example, the sensor device 106 can include onboard processing logic that can determine when the absorbent article 102 has reached a threshold saturation level and thus requires changing based on a color property or other measured property of color changing wetness indicator provided on or within the absorbent article. Based on a determination that the threshold saturation level has been reached, the sensor device 106 can be configured to transmit a notification message to the external user device 108 that indicates the absorbent article 102 has reached the threshold saturation level. The external user device 108 can further render the notification using an appropriate rendering mechanism (e.g., as a visual notification rendered via a display, as an audible alarm, or the like).

In this regard, the sensor device 106 and the external user device 108 can include suitable communication hardware and/or software that provides for wireless (and/or wired) communication the respective devices. For example, the sensor device 106 and the (at least one) external user device 108 can be communicatively coupled via one or more networks (e.g., a personal area network (PAN), a local area network (LAN), a wide area network (WAN) such as the Internet, and the like). The sensor device 106 and the external user device 108 can employ various suitable wired and/or wireless communication technologies to communicate information therebetween. For example, some suitable communication technologies/protocols can include but are not limited to: Bluetooth®, Bluetooth low energy BTLE®, Mesh (e.g., IEEE 802.15.4), WiFi (e.g., IEEE 802.15.10), communication incorporating all or any portion of IEEE 802 or similar communication standards, RFID technology, near field communication (NFC), 3G communication, 4G communication, 5G communication, Backscatter communication, light communication, audio/sound communication, harvesting protocol communication (e.g., a metadata harvesting protocol), and the like. Other communications protocols or combinations of communications protocols (e.g., a Bluetooth/Mesh combined protocol) can be employed. Additionally, or alternatively, an acoustic or optical broadcasting can be employed. Although system 100 depicts a single external user device 108, it should be appreciated that the sensor device 106 can be configured to communicate with a plurality of external devices of varying types (e.g., user devices, routers, monitors, other sensor devices, server devices, cloud-based systems, etc.).

In accordance with various embodiments, system 100 can employ an activation protocol that facilitates preventing use of the sensor device 106 with unauthorized products. For example, the activation protocol can facilitate ensuring that the sensor device 106 is only used with and/or works as intended with absorbent articles of a certain manufacturer and/or brand. The activation protocol can require one or more functionalities of the system to be activated based on receipt and/or validation, by the sensor device 106, external user device 108 and/or other portion of the system (e.g., server device, cloud, software, edge computing, other sensing hardware) of an activation code 105, wherein the activation code is received and/or otherwise made accessible based on use of the sensor device 106 with authorized absorbent articles and/or purchase of the authorized absorbent articles (and/or other authorized products). The one or more functionalities of the sensor device 106 that can require activation using the activation protocol can include for example (but are not limited to) the operation of, or the enhanced operation of: one or more sensors of the sensor device, processing hardware and/or software that provides for processing of the captured sensor data and/or computer executable components, storing logic that provides for storing captured and/or processed sensor data in a memory, a communication protocol (e.g., bidirectional communication) that provides for transmitting the captured and/or processed sensor data to an external user device, external server device, cloud-based system, edge-based system, another device remote from the sensor device, a software application (e.g., connected care application), one or more computer executable components (e.g., communication component, code capture component, a validation component, a sensor activation control component, a feedback processing component, a notification component, a use tracking component, an ordering component, and a reward component) and/or a restriction protocol to restrict any of the foregoing functionalities to use of the sensor device with one or more absorbent articles made by the same manufacturer and combinations thereof. In this regard, without activation of the one or more functionalities of the system using the techniques described herein, one or more system components (e.g., the sensor device, the computer executable components, the software application) will not be fully functional and thus cannot perform at least some of its intended functions, such detecting, tracking and/or reporting wetness levels, activity levels and the like.

The activation code may be in the form of letters, numbers, shapes, symbols, designs and combinations thereof. In some embodiments, the activation code 105 can be or be embodied within a visual identifier (e.g., symbol, numeric code) 304 that is printed or otherwise formed on the absorbent article packaging, more preferably on an interior surface of packaging, and/or on one or more of the absorbent articles included in package of absorbent articles. For example, the absorbent article packaging can include but is not limited to: a film package, a box, a bag, a container, a wrap, internal packaging materials, and the like. The visual identified may be provided on any portion of the packaging that contains the absorbent article 102 or a set of absorbent articles.

Figure 3A:
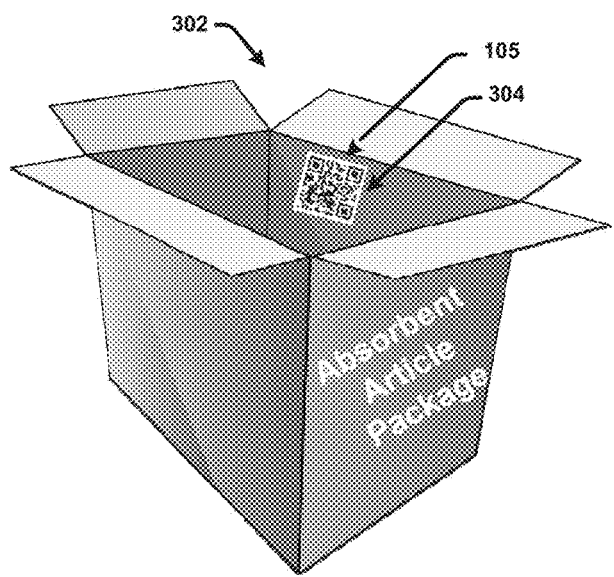
FIGS. 3A and 3B illustrate example placement of activation/identification codes on authorized products for use with sensor devices in accordance with one or more embodiments of the disclosed subject matter.
Figure 3B:
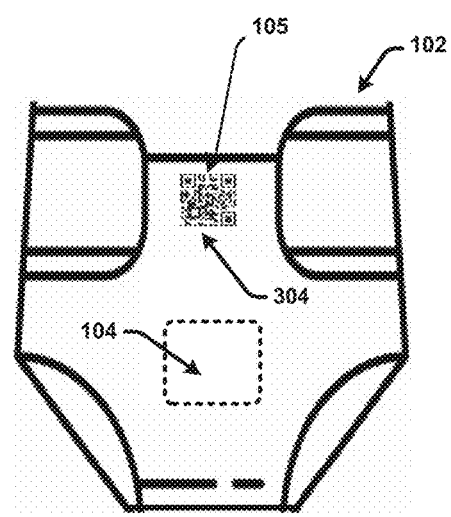

In some implementations, the activation code can be or be embodied within a visual identifier 304 in the form of a barcode (e.g., a QR® code) that is printed on or within the absorbent article packaging and/or one or more absorbent articles included within a package containing a plurality of absorbent articles. For example, FIGS. 3A and 3B illustrate example placement of activation/identification codes on authorized products for use with sensor devices (e.g., sensor device 106). As shown in FIG. 3A, in some implementations, a barcode 304 can be printed on or within an absorbent article package 302 that contains one or more absorbent articles authorized for use the sensor device 106. With this implementation, a consumer will need to purchase and open the packaging of the authorized product in order to reveal the barcode 304. In another implementation, the barcode 304 can be printed on a portion of the absorbent article 102, as shown in FIG. 3B. For example, each absorbent article to be used with the sensor device 106 can include a different barcode 304 that corresponds to a different activation code. Alternatively, one of the absorbent articles in the package (e.g., the first/top absorbent article in the stack) can include the barcode 304, wherein the barcode 304 corresponds the activation code required for activating the one or more functionalities of the system 100 for use with all the absorbent articles included in the package.

With reference to FIGS. 3A and 3B in view of FIG. 1, using a camera of the external user device 108 or a camera and/or an image sensor of the sensor device 106 itself (e.g., in implementations in which the sensor device comprises a camera and/or image sensor), the QR code 304 can be scanned to extract the activation code. In other implementations, the QR code 304 can be replaced with a traditional barcode, or another type of visual code, symbol or identifier. For example, in some implementations, the QR code can be replaced a unique alphanumeric code that is printed in visible region on or within the absorbent article package 302 and/or on the absorbent article itself (see FIG. 1). With these implementations, the alphanumeric code can be manually entered at the external user device 108 using a suitable input device of the external user device (e.g., a touchscreen, a keypad, etc.). In other non-limiting examples, the activation code can be embodied within a RFID tag that is located on or within the absorbent article package 302 and/or on or within one or more absorbent articles included within a package of absorbent articles. With these implementations, the activation code can be extracted from the RFID tag using an RFID tag reader of the external user device 108, the sensor device 106, or auxiliary device (e.g., a separate RFID tag reader communicatively coupled to the external user device and/or the sensor device).

In some embodiments, regardless of the manner in which the external user device receives the activation code, the external user device can send the activation code to the sensor device using a wired or wireless communication means. The sensor device can further activate the one or more functionalities of the sensor device based on receipt and/or validation of the activation code. Similarly, in embodiments in which the sensor device 106 itself captures and/or otherwise extracts the activation code as printed or provided on or within the absorbent article packaging and/or one or more absorbent articles included in a package, the sensor device can further be configured to activate the one or more functionalities of the system based on capture and/or validation of the activation code.

Figure 4:
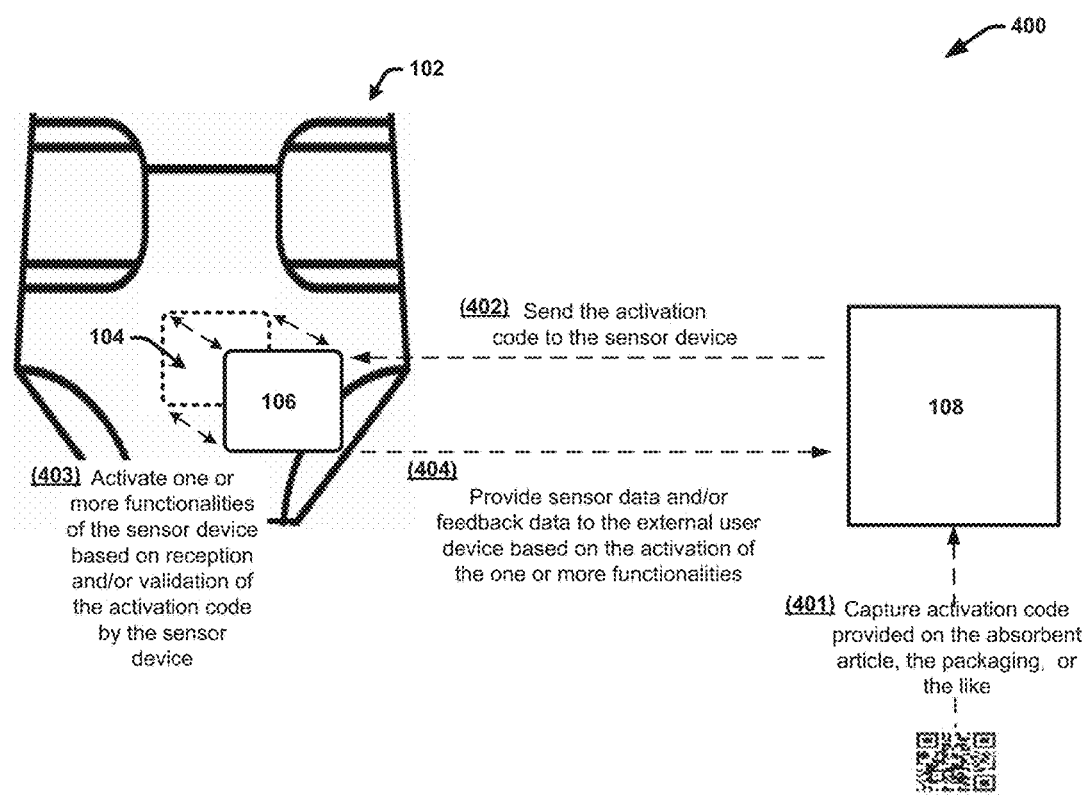
FIG. 4 presents a high-level flow diagram of an example activation process for coupling activation of a sensor device with use of authorized products in accordance with one or more embodiments of the disclosed subject matter.

For example, FIG. 4 presents a high-level flow diagram of an example activation process 400 provided by system 100 for coupling activation of a sensor device (e.g., sensor device 106). In accordance with activation processes 400, at 401 the external user device 108 can capture an activation code provided on an absorbent article, absorbent article packaging or the like, such as an activation code embodied within a QR code 304. At 402, the external user device 108 can further send the activation code to the sensor device 106. For example, in some implementations, the external user device 108 can send the activation code to the sensor device 106 in association with an activation request to activate the one or more functionalities of the sensor device 106. At 403, the sensor device 106 can further activate one or more functionalities of the sensor device 106 based on receipt and/or validation of the activation code. Various techniques for validating the activation code by the sensor device 106 are discussed in greater detail infra with reference to FIG. 9. At 404, based on activation of the one or more functionalities of the sensor device, the sensor device 106 can then provide the external user device 108 with the sensor data (e.g., raw sensor data, sensor measurement data, etc.) and/or sensory feedback data (e.g., usage data and/or activity data).

Figure 5:
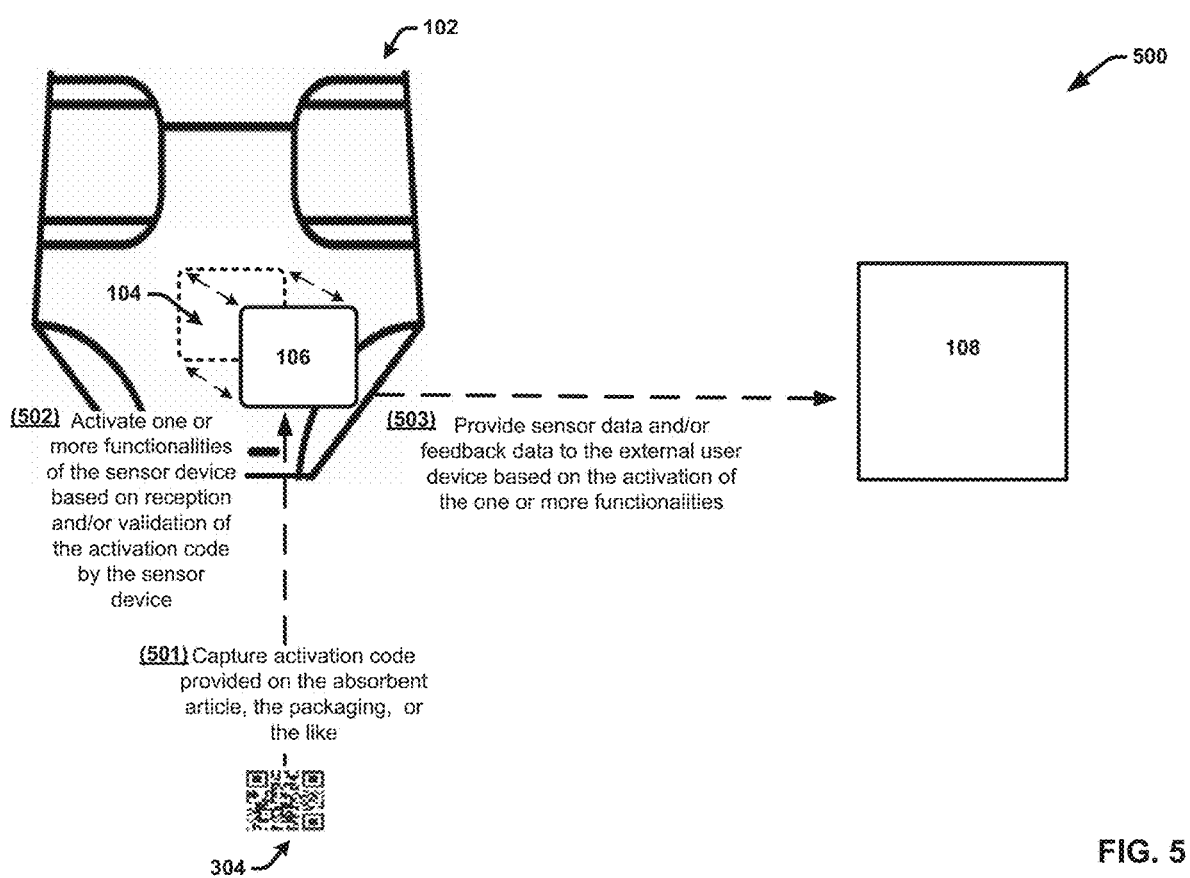
FIG. 5 presents a high-level flow diagram of another example activation process for coupling activation of a sensor device with use of authorized products in accordance with one or more embodiments of the disclosed subject matter.

FIG. 5 presents a high-level flow diagram of another example activation process 500 provided by system 100 for coupling activation of a sensor device (e.g., sensor device 106) with use of authorized products. Repetitive description of like elements employed in respective embodiments is omitted for sake of brevity.

Activation process 500 is similar to activation processes 400 with the difference being that the sensor device 106 itself can capture the activation code as opposed to the external user device 108. In accordance with processes 500, at 501, the sensor device 106 can capture an activation code provided on an absorbent article, absorbent article packaging or the like, such as an activation code embodied within a QR code 304. For example, the QR code 304 can be scanned using a camera or image sensor of the sensor device 106 to extract the activation code represented by the QR code 304. The activation code can be or be embodied within another type of visual identifier 304 (e.g., symbol, image, pattern, identifier, color, etc.), and the sensor device 106 can capture the visual symbol, image, pattern, identifier, etc., using a camera or image sensor of the sensor device. At 502, the sensor device 106 can further activate one or more functionalities of the sensor device, or other portion of the system, based on receipt and/or validation of the activation code. At 503, based on activation of the one or more functionalities, the sensor device 106 can then provide the external user device 108 with the sensor data and/or sensory feedback data.

Figure 6:
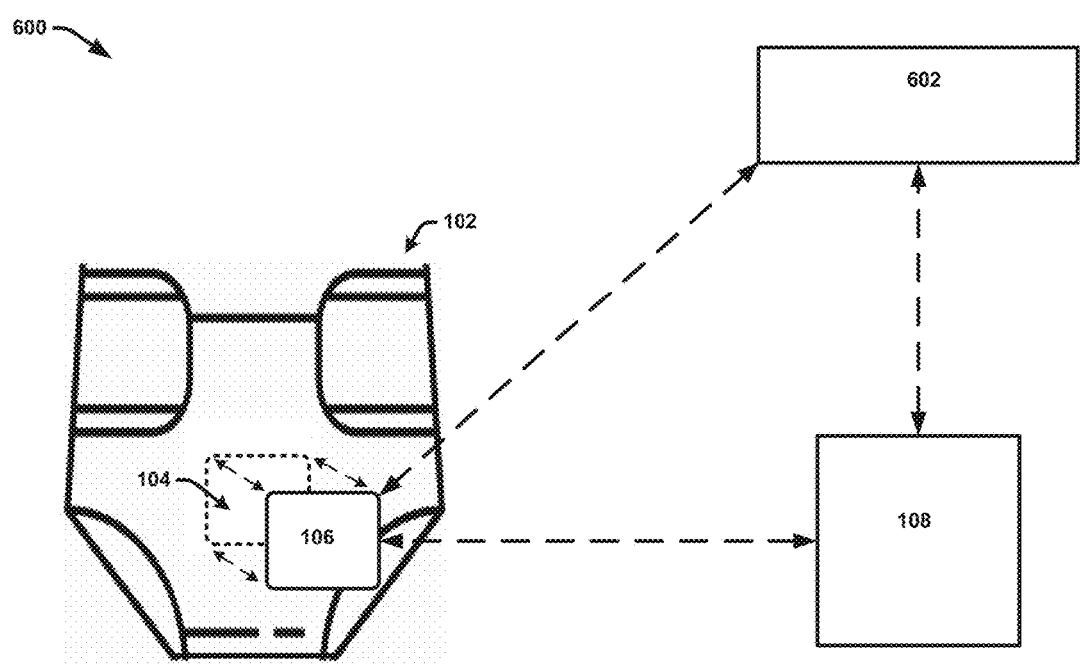
FIG. 6 illustrates a block diagram of another example, non-limiting system for coupling activation of a sensor device with use of authorized products in accordance with one or more embodiments of the disclosed subject matter.

FIG. 6 illustrates a block diagram of another example, non-limiting system 600 for coupling activation of a sensor device with use of authorized products. System 600 includes same or similar features and functionalities as system 100 with the addition of an external server device 602. Repetitive description of like elements employed in respective embodiments is omitted for sake of brevity.

System 600 includes sensor device 106, external user device 108, and external server device 602. These devices can be communicatively coupled to one another, either directly or indirectly (e.g., via another device), using one or more wired and/or wireless communication technologies described herein. For example, in some embodiments, the external server device 602 and the sensor device 106 can be configured to communicate with one another using one or more WAN wireless communication technologies. For instance, the external server device 602 can communicate directly with the sensor device 106 to provide firmware updates over the air, to receive sensory feedback data from the sensor device 106, and the like. In other non-limiting examples, the external server device 602 and the sensor device can communicate indirectly through the external user device 108.

In one or more embodiments, the external server device 602 can facilitate the sensor device activation process. For example, in some implementations, the external server device 602 can be or correspond to one or more cloud-based server devices or edge-based systems configured to control generation and/or provision of activation codes to sensor devices (e.g., sensor device 106) required for activation of the one or more functionalities of the sensor device 106 or other portion of the system. With these implementations, the external server device 602 can provide the external user device 108 with an activation code required for activating the one or more functionalities of the sensor device 108 based on one or more defined events that verify the sensor device 16 will be used and/or is being used with authorized products. The external user device 108 can further provide an activation code received from the external server device 602 to the sensor device 106 to activate the one or more functionalities.

Figure 7:
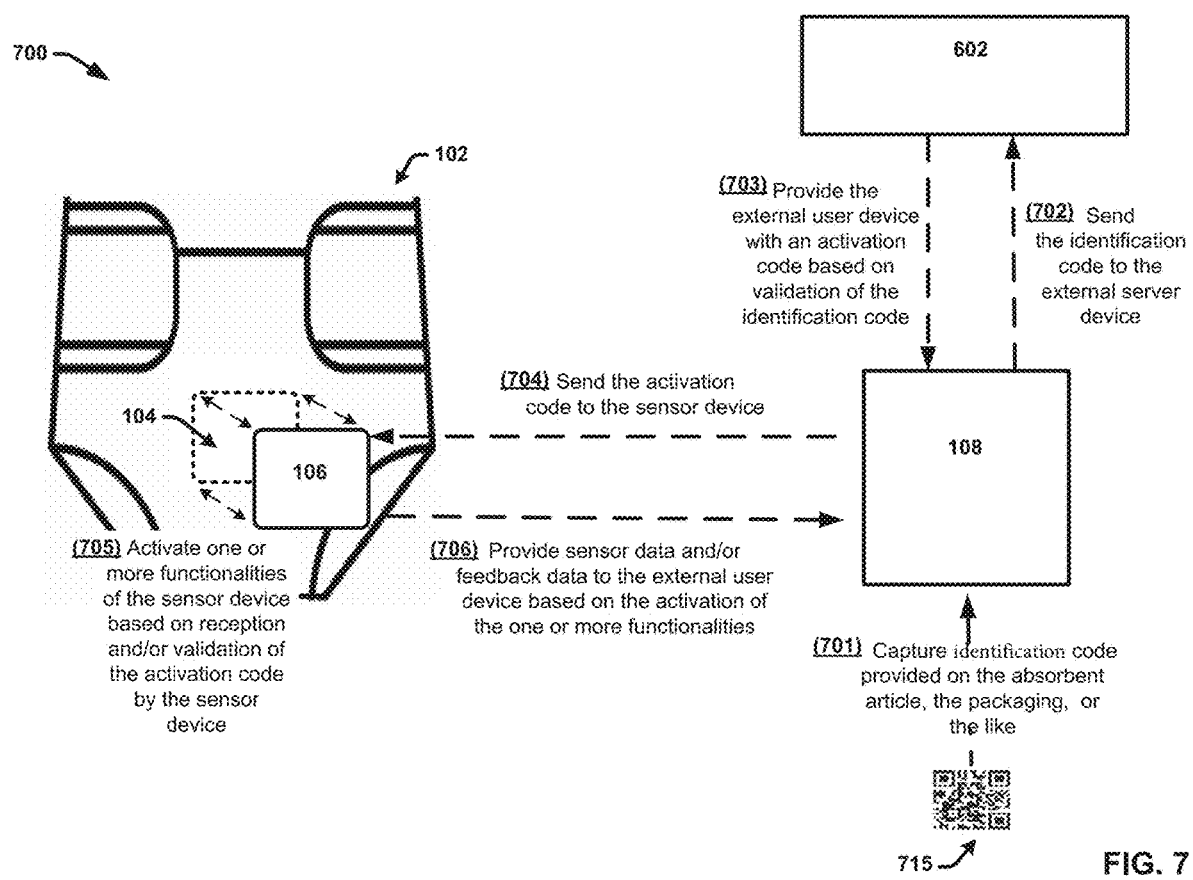
FIG. 7 presents a high-level flow diagram of another example activation process for coupling activation of a sensor device with use of authorized products in accordance with one or more embodiments of the disclosed subject matter.

For example, FIG. 7 presents a high-level flow diagram of an example activation process 700 provided by system 600 for coupling activation of a sensor device with use of authorized absorbent articles. Repetitive description of like elements employed in respective embodiments is omitted for sake of brevity.

In accordance with activation process 700, a unique identification code 715 (as opposed to the activation code) can be printed and/or otherwise provided on within the absorbent article packaging and/or the absorbent itself. For example, similar to the activation code, the unique identification code can also be or be embodied within a visual symbol or code (e.g., a barcode, a QR code, an alphanumeric identifier, etc.), an RFID tag, and the like. For example, in some embodiments, a QR code can be or correspond to an identification code (as opposed to an activation code). With these embodiments, at 701, the external user device 108 can capture, extract and/or otherwise receive the identification code 715 as provided on an absorbent article, the packaging or the like, using the techniques described supra.

At 702, the external user device 108 can further send the captured/received identification code to the external server device 602 (e.g., via a network such as the Internet or another suitable communication network) in association with a request to validate the identification code. Based on receipt of the identification code, the external server device 602 can employ various techniques to determine whether the identification code is valid, invalid or otherwise expired based on receipt of the identification code in association with the validation request. For example, in some embodiments, the external server device 602 can maintain a list of valid identification codes (e.g., in memory accessible to the external server device 602). The external server device 602 can further determine that an identification code is valid if the identification code is included in the list. The external server device 602 can also remove previously used identification codes or otherwise declare them as expired to ensure valid identification code cannot be reused to reactivate the same sensor device 106 and/or to activate/reactivate a different sensor device. Other techniques that can be used by the external server device 602 to determine whether a received identification code is valid are discussed in greater detail with reference to FIG. 16.

At 703, based on a determination that the identification code is valid, the external server device 602 can provide the external user device 108 with an activation code required for activation of the one or more functionalities of the sensor device 106. At 704, the external user device 108 can then send the activation code to the sensor device 106, and at 705, the sensor device 106 can activate one or more functionalities of the sensor device 106 based on receipt and/or validation of the activation code. At 706, the sensor device 106 can further provide the external user device 108 with sensor data and/or feedback determined based on the sensor data based on activation of the one or more functionalities.

With reference again to FIG. 6, in various additional embodiments, the external server device 602 can facilitate provision of a variety of ancillary services to customers associated with use of the sensor device 106 via a mobile device application and/or web-based platform (e.g., a website, a web-application, or the like). For example, in some implementations, the mobile device application and/or web-based platform system can facilitate purchasing/ordering authorized products for use with the sensor device 106 via the mobile device application, website or the like. The external sever device 602 can further receive confirmation when the external user device 108 and/or user account associated with the sensor device 108 has purchased/ordered an authorized product in association with use of the mobile device application, website or the like. The external server device 602 can further provide the external user device 108 with an activation code for activating the sensor device 108 based on confirmation that the user has ordered/purchased an authorized product (e.g., absorbent articles and other products) using. For example, in some implementations, the external server device 602 can send the activation code to the external user device 108 as a text message, push notification, email, or the like. In other implementations, the external server device 602 can issue or otherwise associate the activation code with a user account established for the user with the external server device 602 (e.g., accessed via an application executed on the external user device, a web-application, a website, or another suitable platform). With these implementations, the external user device 108 can access and retrieve the activation code for provision to the sensor device in association with logging into their account (e.g., via the mobile device application as executed on the external sensor device, or the like).

In non-limiting examples, the external server device 602 can provide the external user device 108 and/or a user account associated with the sensor device 106 with an activation code and/or other rewards (e.g., coupons, reward points, extended activation times for the sensor device, additional feature activation for the sensor device, etc.) based on various other types of user activity associated with use of the application/website. For example, such other user activity can include using interactive and/or social media features associated with the application, providing manual input regarding behavior of the wearer, wearer habits (e.g., feeding habits, moods, etc.), appearance of the wearer, and other relevant data about the wearer.

Figure 8:
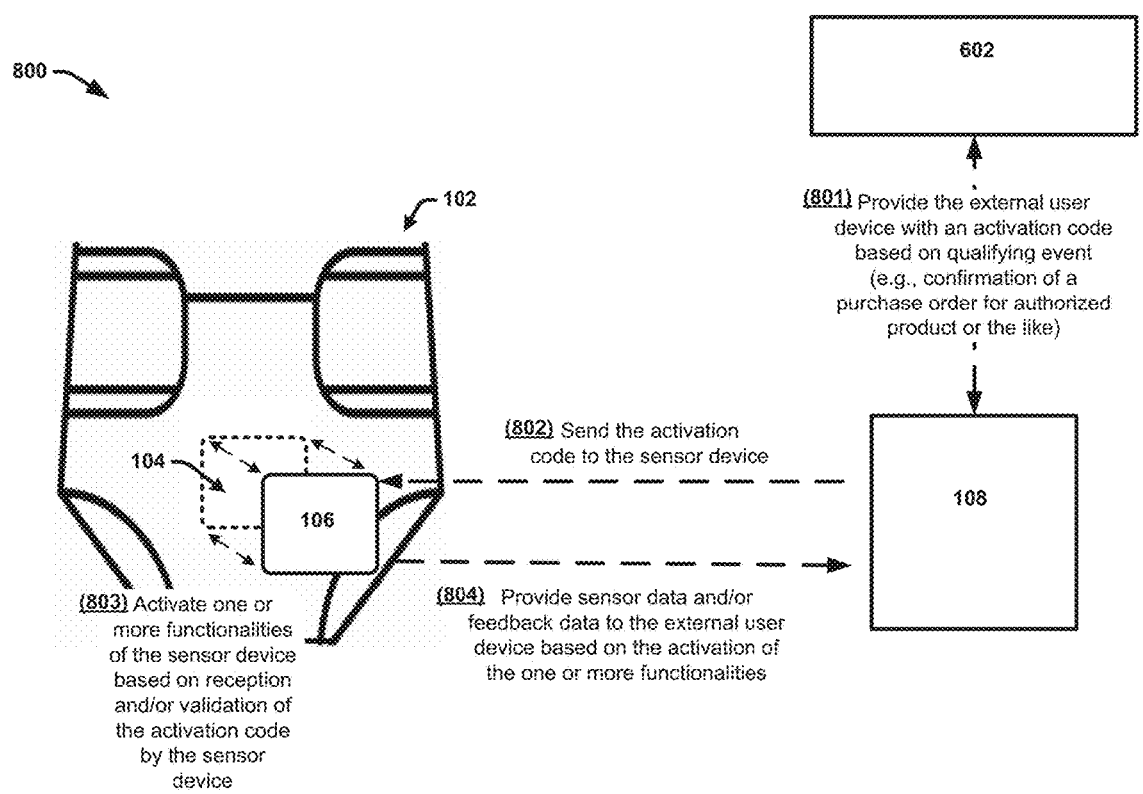
FIG. 8 presents a high-level flow diagram of another example activation process for coupling activation of a sensor device with use of authorized products in accordance with one or more embodiments of the disclosed subject matter.

For example, FIG. 8 presents a high-level flow diagram of another example activation process 800 provided by system 600 for coupling activation of a sensor device (e.g., sensor device 106) with use of authorized products in accordance with one or more embodiments of the disclosed subject matter. Repetitive description of like elements employed in respective embodiments is omitted for sake of brevity.

At 801, the external server device 602 can provide the external user device 108 with an activation code based on a qualifying event. For example, in some implementations, the qualifying event can be a determination that a user/user account associated with the external device 108 and/or the sensor device 106 has purchased/ordered an authorized product for use with the sensor device 106. In another example, the qualifying event can be enrollment in a monthly product delivery service for a defined amount of authorized product. In another example, the qualifying event can be based on provision of user reported feedback associated with use of the sensor device 106 via the mobile device application and/or web-based platform. Various other qualifying events associated with use of the mobile device application and/or web-based platform serviced by the external server device 602 are also envisioned.

In some embodiments, the external server device 602 can provide the activation code to the external user device 108 in the form of a text message, push notification, email, or the like. Additionally, or alternatively, the external server device 602 can associate the activation code with a user account associated with the external user device 108 and/or the sensor device. With these embodiments, the activation code can be retrieved by the external user device 108 in association with logging into the user account and accessing the activation code. Once the activation code is received and/or retrieved by the external user device 108, activation process 800 can then proceed in same or similar fashion as activation process 700. In this regard, at 802, the external user device 108 can send the received/retrieved activation code to the sensor device 106. At 803 and the sensor device 106 can activate one or more functionalities of the system based on receipt and/or validation of the activation code, and at 804, based on activation of the one or more functionalities, the sensor device 106 can provide the external user device 108 with the sensor data and/or feedback determined based on the sensor data.

Figure 9:
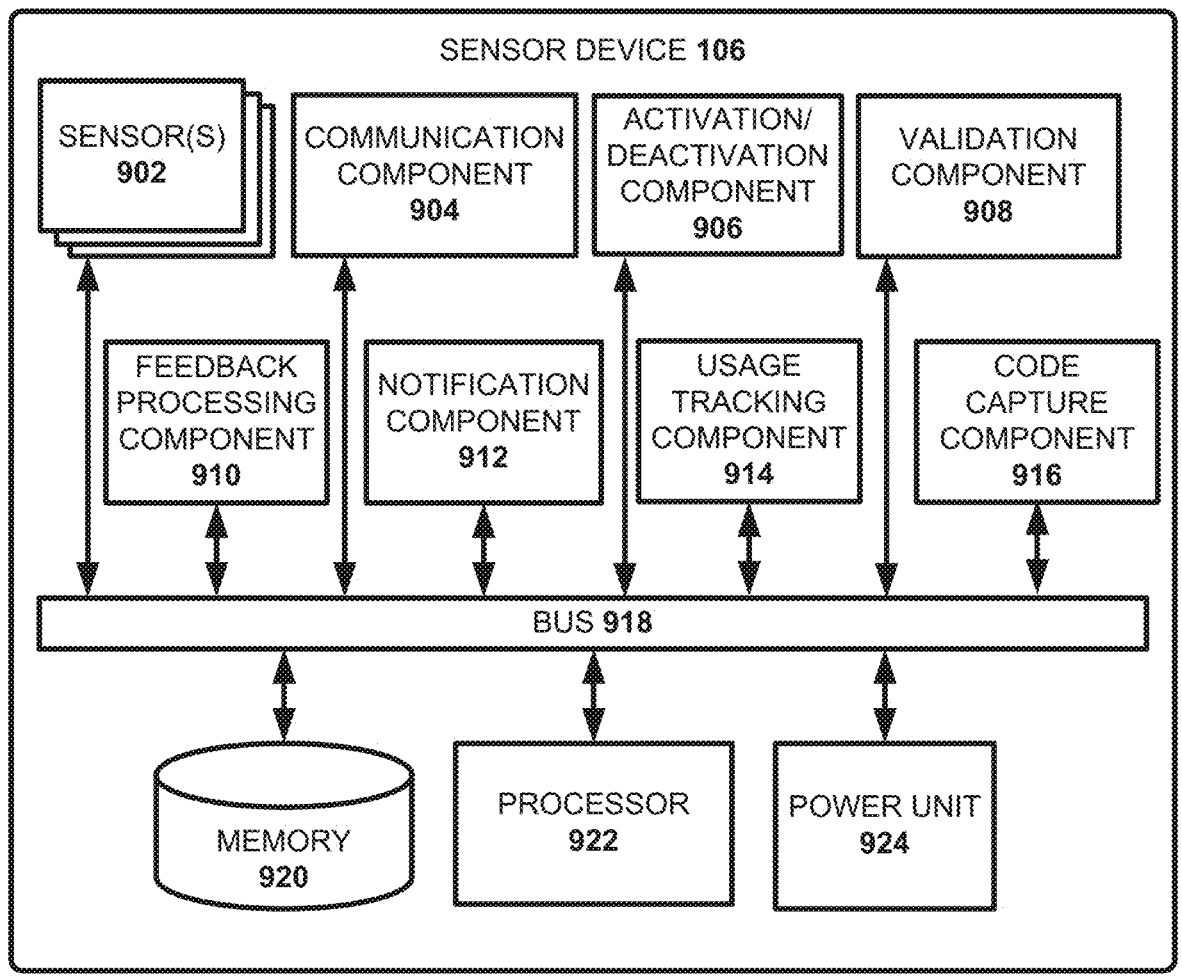
FIG. 9 illustrates a block diagram of an example sensor device configured to couple activation of the sensor device with use of authorized products in accordance with one or more embodiments of the disclosed subject matter.

With reference now to FIG. 9, illustrated is a block diagram of an example sensor device (e.g., sensor device 106) configured to couple activation of the sensor device with use of authorized products. Various aspects of devices, systems, apparatuses or processes explained in this disclosure can constitute machine-executable component(s) embodied within machine(s), e.g., embodied in one or more computer readable mediums (or media) associated with one or more machines. Such components, when executed by the one or more machines, (e.g., computers, computing devices, virtual machines, etc.) can cause the machines to perform the operations described.

For example, in the embodiment shown, the sensor device 106 can include one or more sensors 902, a communication component 904, an activation/deactivation component 906, a validation component 908, a feedback processing component 910, a notification component 912, a use tracking component 914, and a code capture component 916, one or more of which can respectively be or include computer/machine-executable components and instructions. The sensor device 106 can also include at least one memory 920 configured to store the computer/machine-executable components and instructions. The sensor device 106 can also include at least one processor 922 (e.g., a microprocessor) to facilitate operation of the computer executable components and instructions by the sensor device 106. The sensor device 106 can further include a power unit 924 that provides for powering the various electrical components of the sensor device 106. The sensor device 106 can further include a device bus 916 that couples the various components of the sensor device 106, including, but not limited to: the one or more sensors 902, the communication component 904, the activation/deactivation component 906, the validation component 908, the feedback processing component 910, the notification component 912, the use tracking component 914, the code capture component 916, the memory 920, the processor 922 and the power unit 924.

It should be appreciated that in some embodiments, one or more of these components can be removed from the sensor device 106. For example, in some embodiments, the disclosed techniques for coupling activation of the sensor device 106 with use of authorized absorbent articles can be implemented without all of the components shown in FIG. 9. One or more of these components shown in FIG. 9 can executed by the external user device 108 and/or the external server device 602.

In various embodiments, the one or more sensors 902 formed on or within a housing of the sensor device (e.g., housing 202) and provide for sensing, detecting or otherwise capturing sensor data regarding usage of an absorbent article to which the sensor device 106 is designed to be attached, and/or activity of the wearer. For example, as discussed with reference to FIGS. 1, 2A and 2B, in various embodiments, the one or more sensors 902 can include one or more optical sensors having any of the features or functionalities described with respect optical sensors 206 and vice versa. Some examples of optical sensors across a range of wavelengths are: electron tube detectors, photosensors, photomultiplier tubes, phototubes, photodetectors, opto-semiconductor detectors, photodiodes, photomultipliers, image sensors, infrared detectors, thermal sensors, illuminance sensors, visible light sensors and color sensors. In some implementations, the sensor device 106 can also include a light source (e.g., light source 208), such as a light emitting diode (LED), organic light emitting diode (OLED), an incandescent light bulb, thermionic light emission, luminescence (e.g., among others, fluorescence, chemilluminescence, electroluminescence (e.g., LED), for emitting light onto an area, the wavelength or spectrum of which is to be assessed by the optical sensor. The optical sensor in some color detecting embodiments can be optimized for assessing a color of a color-changing indicator. The optical sensor can be sensitive to visible and non-visible light. In various embodiments, ultraviolet (UV), visible infrared and near infrared wavelengths may be used.

The one or more sensors 902 can include any of the one or more sensors 103 described above (e.g., optical, motion, image, biosensor, etc.) with respect to FIG. 1.

The communication component 904 can provide for communicatively coupling the sensor device 106 with one or more external devices, such as external user device 108, external sever device 602, and/or various other devices remote (e.g., physically remote) from sensor device 106. In this regard, the communication component 904 can include software, hardware, or a combination of software and hardware that is configured to facilitate performance of wireless (and/or wired) communications between the sensor device and the one or more external devices. For example, the communication component 904 can include and/or be configured to control operation of one or more transmitters/receivers of the sensor device 106 to provide for transmitting information to the one or more external devices and/or receiving information from the one or more external devices.

The communication component 904 can be configured to facilitate wireless communication with the one or more external devices (e.g., the external user device 108) using a variety of wireless communication protocols. For example, in one or more embodiments, the communication component 904 can communicate with an external device using a Bluetooth® communication protocol, a near-field communication (NFC) protocol, or another type of communication protocol over a PAN or a LAN, (e.g., a Wi-Fi network) that can provide for communication over greater distances than NFC protocol or that can provide various advantages (such as increased security). Other communication protocols that can be employed by communication component 904 to communicate with an external device can include, but are not limited to: a Session Initiation Protocol (SIP) based protocol, a Zigbee® protocol, a RF4CE protocol, a WirelessHART protocol, a 6LoWPAN (IPv6 over Low power Wireless Personal Area Networks) protocol, a Z-Wave protocol, an ANT protocol, an ultra-wideband (UWB) standard protocol, a cellular communications protocol (e.g., second, third, fourth and fifth Generation Partnership Project (GGP) protocols, Long Term Evolution (LTE), protocols), machine type communication (MTC) protocols, Narrowband Internet-of-things (NB-IoT) protocols, other radio frequency (RF) communication protocols, non-RF communication protocols (e.g., induction based, optical based, audio based, etc.) and/or other proprietary and non-proprietary communication protocols.

The activation/deactivation component 906 can provide for activating and/or deactivating one or more functionalities of the sensor device. For example, as discussed above, the one or more functionalities can include but are not limited to: activation of processing hardware and/or software that provides for processing of the captured sensor data, activation of storing logic that provides for storing captured and/or processed sensor data in memory of the sensor device, and/or activation of a communication protocol (e.g., bidirectional communication) that provides for transmitting the captured and/or processed sensor data to the external user device or another device remote from the sensor device. In this regard, without activation of the one or more functionalities of the sensor device 106 by the activation/deactivation component 906 using the techniques described herein, the sensor device will not be fully functional and thus cannot perform at least some of its intended functions, such detecting, tracking and/or reporting information regarding wetness levels, activity levels and the like.

In some embodiments, the activation/deactivation component 906 can activate one or more functionalities of the sensor device 106 based on receipt (e.g., as received from an external user device 108) and/or capture of an activation code by the sensor device 106 (e.g., as captured via the code capture component 916). Additionally, or alternatively, the activation/deactivation component 906 can activate the one or more functionalities of the sensor device 106 based on validation of the activation code. With these embodiments, sensor device 106 can include validation component 908 to provide one or more validation mechanism for validating an activation code received from the external device 108 and/or captured by the sensor device directly (e.g., via the code capture component 916).

For example, in some embodiments, the sensor device 106 can store information in memory 920 identifying one or more predefined (secret) activation codes and/or (secret) activation code properties. With these embodiments, the activation/deactivation component 906 can be configured to only activate the one or more functionalities of the sensor device 106 if the received activation code corresponds to (e.g., matches) the one or more predefined activation codes and/or if the received activation code has the defined activation code properties. In further non-limiting examples, the activation code as received from the external user device 108 and/or otherwise captured by the sensor device directly (e.g., via cod capture component 916) can be encrypted with a secret encryption key or the like that the sensor device 106 is preconfigured with (e.g., in memory 920). With these examples, the validation component 908 can be configured to determine whether the activation code is valid based on an ability to decrypt the activation code using the secret encryption key (e.g., valid if capable of being decrypted).

In another non-limiting example, the validation component 908 can validate the activation code based on a combination of the activation code and a secret code, identifier or signal 105S provided on or within the absorbent article 102. The secret code 105S may not be visible to the user without damaging the article or may be visible but not apparent as a code (e.g., a mark on a graphic). With these implementations, the one or more sensors 902 include one or more sensors configured to capture and/or extract the secret code, identifier or signal from the absorbent article. For example, in some embodiments, the one or more sensors 902 can include a camera or image sensor that can capture and/or otherwise extract the secret code/identifier as printed or otherwise provided on a layer of the absorbent article 102 that is not visible to the user. With these embodiments, the activation/deactivation component 906 can be configured to activate the one or more functionalities of the sensor device 106 based on a combination of the activation code and the secret extracted code. For example, in one implementation, the activation/deactivation component 906 can be configured to only activate the one or more functionalities of the sensor device if the validation component 908 determines that the activation code is valid based on the activation code corresponding to or matching the secret code match. In another implementation, the secret code can be encrypted, and the activation code can correspond to an encryption key, or vice versa. The validation component 908 can further be configured to validate the activation code if the validation component 908 can decrypt the secret code using the activation code, or vice versa.

With these embodiments, the correct combination of the secret code and the activation code can further facilitate restricting use of the activated sensor device with only specific absorbent article or set of absorbent articles, as well as ensuring that an activation code cannot be reused to activate the sensor device for use with unauthorized products. For example, in one implementation, each absorbent article can have a different unique secret code provided therein that is matched/paired with a single activation code printed on visible portion of the absorbent article. In another implementation, an entire set of absorbent articles included in a package can have the same unique secret code that is paired with a single activation code provided on or within the packaging and/or one or more absorbent articles included in the package (e.g., the first absorbent article in the stack). In either of these implementations, the sensor device can be configured to deactivate the one or more activated functionalities based on a determination that the combination of the activation code and the secret code has changed or otherwise is no longer recognized as correct (e.g., based on reattachment of the sensor device to a new absorbent article that does not have the correct secret code).

In some embodiments, the sensor device 106 can be configured to send some or all captured sensor data (e.g., raw sensor data and/or digital information corresponding to captured/detected sensor measurement values) to the external user device 108 for processing and/or presentation by the external user device 108. The sensor data can include any measurements, properties, characteristics mentioned above with respect to sensory data feedback. With these embodiments, the external user device 108 can be configured to process and analyze the sensor data to determine and/or infer sensory feedback data based on captured sensor measurements. For example, the external user device 108 can process the sensor data to determine usage and/or activity information discussed above.

Additionally, or alternatively, the feedback processing component can be configured to provide for partial and/or full onboard processing of the sensor data to generate the sensory feedback data (e.g., the input parameters) based on the captured sensor data. For example, in various embodiments, the feedback processing component 910 can be configured to process/analyze the sensor data captured via the one or more sensors using predefined processing logic (e.g., algorithms, heuristics, machine learning models, defined correlations, tracked data correlations, etc.) to determine and/or infer sensory feedback data regarding usage and/or activity information for the wearer.

In some implementations, the communication component 904 can be configured to send the determined/inferred sensory feedback information to the external user device 108 for rendering and/or further processing by the external user device 108 and/or forwarding to the external server device 602 (or another device). The external user device 108 can further be configured to present or otherwise provide the determined information to the user as a real-time notification (e.g., notification when absorbent article is wet and needs changing), as an assessment report, or the like.

In various implementations, the sensor device 106 can include a notification component 912 that can be configured to generate and send notifications to the external device based on detection of defined sensor measurement values and/or based on a determination, by the feedback processing component 910, that a defined event or condition has occurred as determined based on the sensor data. By way of non-limiting example, the notification component 912 can be configured to generate and/or send the external user device 108 a notification that the absorbent article is wet based on a determination that the absorbent article is wet or has reached a defined saturation level. In another non-limiting example, the notification component 910 can generate and/or send the external user device 108 a notification indicating that wearer has woken based on a determination that the wearer's activity level/pattern indicates the wearer is no longer asleep.

In some embodiments, the sensor device 106 can include use tracking component 914 to provide for tracking use of the sensor device 106 with absorbent articles. For example, the use tracking component 914 can be configured to track use information including but not limited to: information regarding timing of attachment and detachment of the sensor device 106 to an absorbent article, duration of activation of the one or more functionalities of the sensor device, number of different absorbent articles the sensor device 106 is attached to/used with when activated, number of wetness events detected per absorbent article to which the sensor device is attached, timing between wetness detection and absorbent article changing, frequency of urination/defecation events, amount of bodily exudates absorbed in the absorbent article, and the like.

The use tracking component 914 and/or the activation/deactivation component 906 can further provide techniques to mitigate use of an activated sensor device, (after activation using one or more of the techniques described herein), with unauthorized products based on the tracked use. For example, in some implementations, the use tracking component 914 can track the activation codes used by the sensor device 106 to activate the one or more functionalities of the system. The activation/deactivation component 906 can further prevent reuse of a previously used code to activate the same sensor device 106 and/or another sensor device.

Additionally, or alternatively, the activation/deactivation component 906 can restrict activation of the one or more functionalities based on use restriction associated with the activation. For example, in some implementations, the use restriction can restrict the amount of time the sensor device remains activated based a single activation code before requiring reactivation using a new activation code. For example, in some implementations, the activation/deactivation component 906 can be configured to deactivate the one or more activated functionalities of the system after passage of a defined duration of time (e.g., 6 hours, 12 hours, 24 hours, one month, three months, etc.) following activation. In another implementation, activation of the one or more functionalities can be associated with a use restriction regarding the number of different absorbent articles (e.g., absorbent articles) to which the sensor device can be attached to and reused with before requiring reactivation using a new activation code. For example, the activation/deactivation component 906 can be configured to deactivate the one or more activated functionalities based on a determination that the sensor device 106 has been used with a maximum number of absorbent articles (e.g., as determined based on number of detachments/reattachments, as determined based on number of wetness events detected, or another defined event). Information regarding restrictions on activation can be stored in memory 920 of the sensor device and/or provided to the external device in association with the activation code.

In some implementations, the use restrictions can be based on the number of absorbent articles included in a package, the duration of time an absorbent article is intended to be worn, user account privileges or the like. For example, in one implementation, an activation code and/or identification code associated with a package of absorbent articles including N number of absorbent articles can be associated with information that instructs the sensor device to remain activated for N number of uses (e.g., attachments to N number of absorbent articles) before requiring reactivation using a new activation code. In another example, an activation code and/or identification code associated with a single absorbent article designed to be worn for a defined time period of M hours (e.g., 12 hours) can be associated with information that instructs the sensor device to remain activated for M hours before requiring a new activation code.

The code capture component 916 can facilitate capturing an activation code using one or more sensors of the sensor device 106. For example, in some embodiments in which the activation code is embodied as a visual symbol, code, image or the like printed on or within the absorbent article package and/or an exterior portion of the absorbent article itself, the code capture component 916 can activate a camera or image sensor of the sensor device to capture and/or extract the activation code. In examples in which the activation code is embodied within an RFID tag associated with the absorbent article/absorbent article packaging, the code capture component 916 can activate an RFID reader of the sensor device to capture and extract the RFID code.

Figure 10:
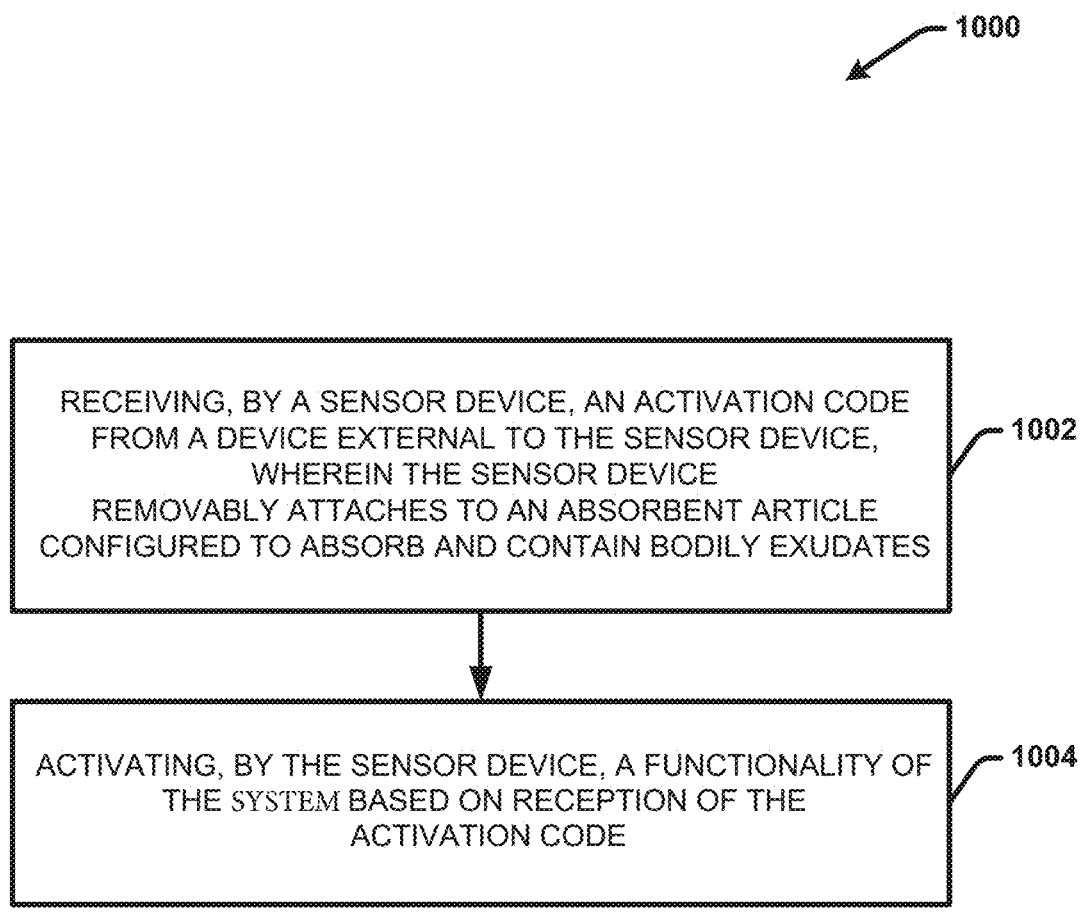
FIG. 10 presents a high-level flow diagram of another example process for coupling activation of a sensor device with use of authorized products in accordance with one or more embodiments of the disclosed subject matter.

The sensor device 106 can further include a suitable power unit to drive the functionality of the sensor device 106 and to provide power to the various electrical components of the sensor device 104. In one or more embodiments, the power unit 924 can include but is not limited to: a rechargeable battery, a non-rechargeable battery, a capacitor, a charge pump, a mechanically derived power source (e.g., microelectromechanical systems (MEMs) device), or an induction component. The sensor device 106 can also include various other device circuitry/hardware to facilitate operation of the various components of the sensor device 106. For example, the sensor device 106 can further include suitable electronic circuitry (e.g., hardware), software, or a combination thereof, that provides for processing of raw sensor measurements representative of a measured property (e.g., a wetness level, an activity level, etc.) as captured via the one or more sensors 902 of the sensor device 106 into a digital signal corresponding to the measured property. For example, such electronic circuitry can include but is not limited to, excitation control elements, amplification elements, analogue filtering elements, data conversion elements, compensation elements, and the like FIG. 10 presents a high-level flow diagram of another example process 1000 for coupling activation of a sensor device with use of authorized products. In various embodiments, process 1000 can be performed by the sensor device 106. Repetitive description of like elements employed in respective embodiments is omitted for sake of brevity. At 1002, a sensor device comprising or operatively coupled to a processor can receive (e.g., via communication component 904) an activation code from a device external to the sensor device (e.g., external user device 108), wherein the sensor device removably attaches to an absorbent article 102 configured to absorb and contain bodily. At 1004, the sensor device can activate a functionality of the sensor device based on receipt of the activation code (e.g., via activation/deactivation component 906).

Figure 11:
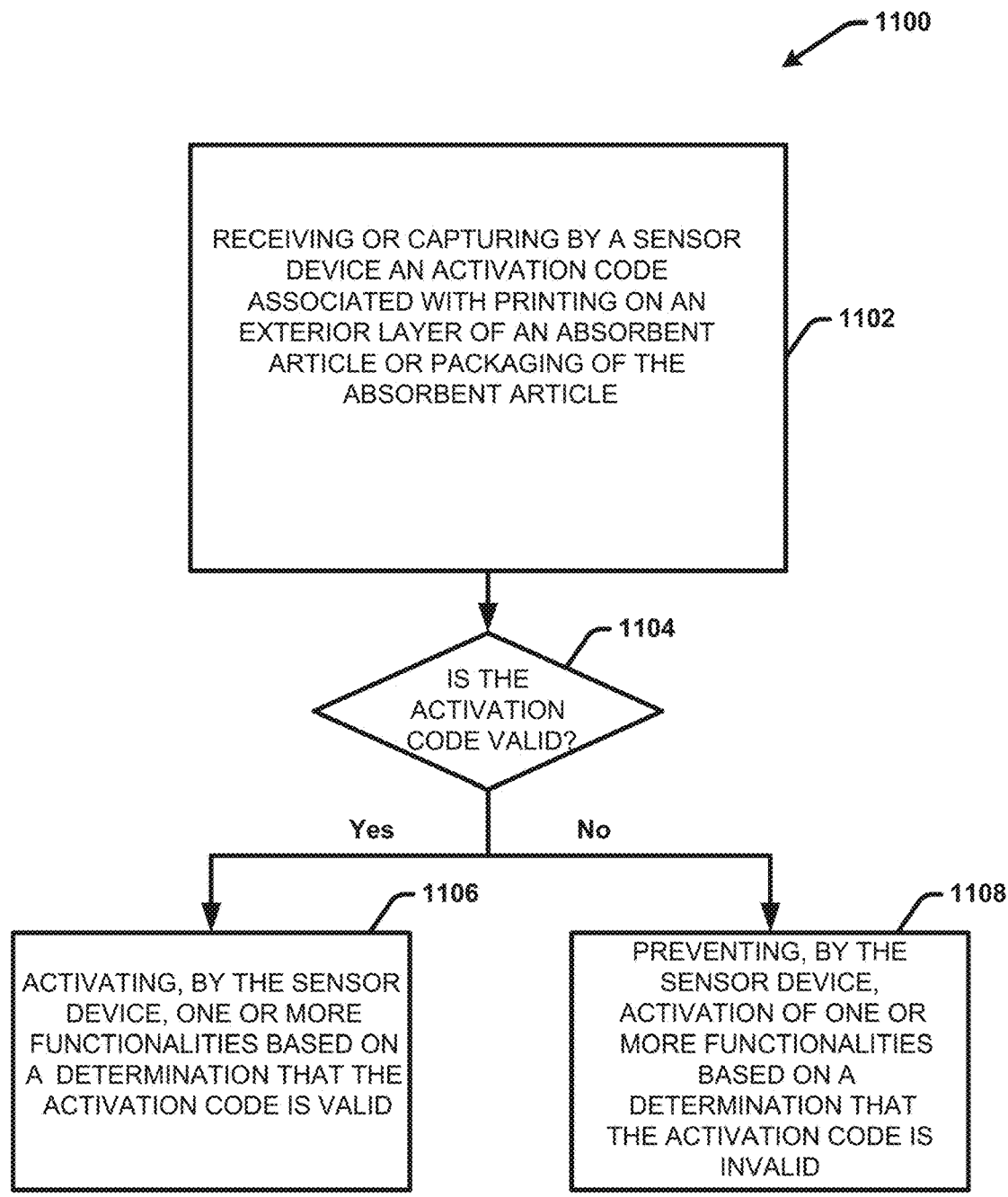
FIG. 11 presents a high-level flow diagram of another example process for coupling activation of a sensor device with use of authorized products in accordance with one or more embodiments of the disclosed subject matter.

FIG. 11 presents a high-level flow diagram of another example process 1100 for coupling activation of a sensor device with use of authorized products that can be performed by the sensor device 106. Repetitive description of like elements employed in respective embodiments is omitted for sake of brevity. At 1102, a sensor device comprising or operatively coupled to a processor can receive (e.g., via communication component 904) or capture (e.g., via code capture component 916) an activation code associated with printing on an absorbent article or packaging of the absorbent article. At 1104, the sensor device can determine whether the activation code is valid (e.g., using validation component 908). If, at 1104, the sensor device determines that the activation code is valid, then at 1106, the sensor device can activate of one or more functionalities of the system (e.g., using activation/deactivation component 906). However, if at 1104 the sensor device determines that the activation code is invalid, then at 1108, the sensor device can prevent activation of one or more functionalities of the system (e.g., using activation/deactivation component 906).

Figure 12:
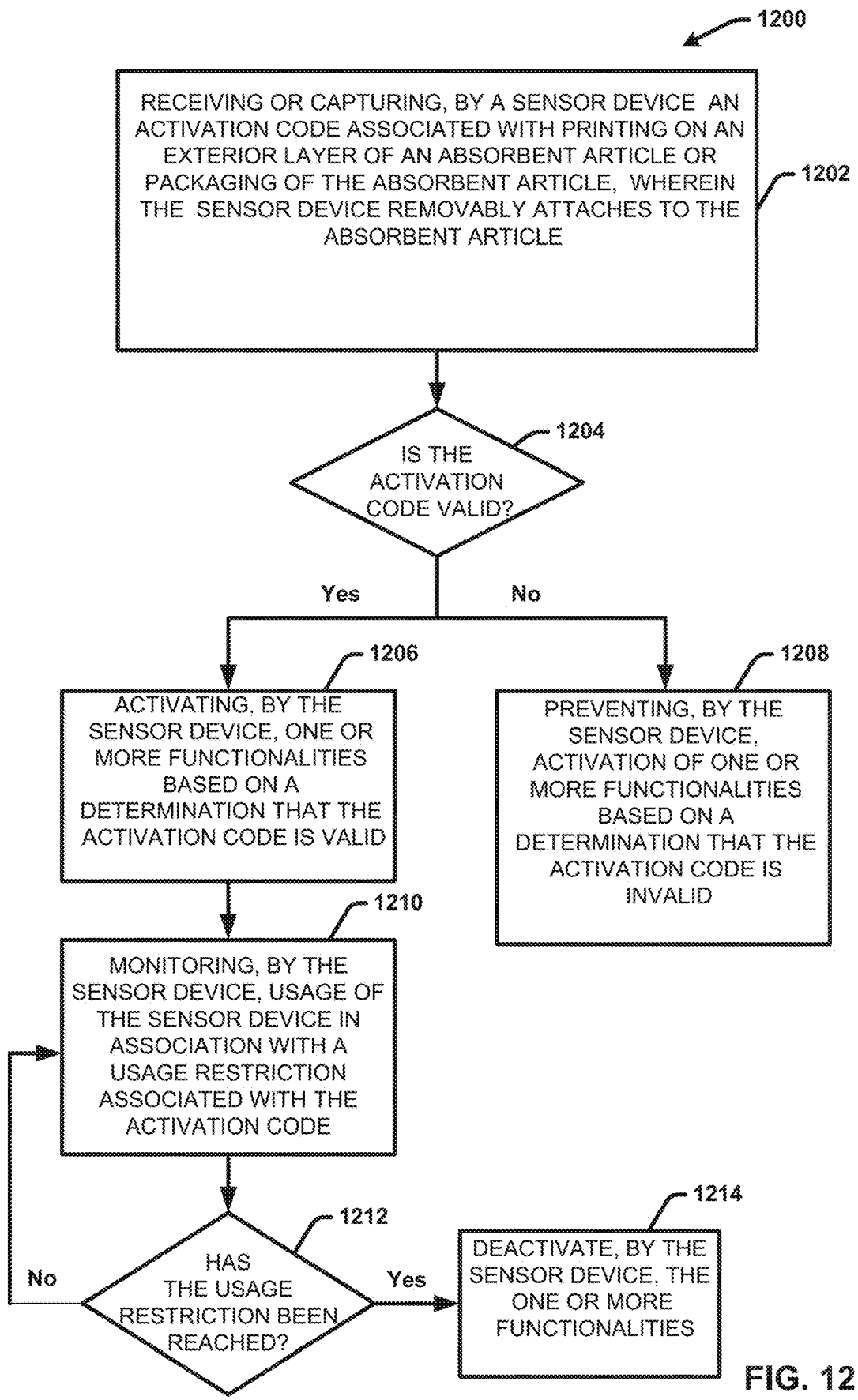
FIG. 12 presents a high-level flow diagram of another example process for coupling activation of the sensor device with use of authorized products in accordance with one or more embodiments of the disclosed subject matter.

FIG. 12 presents a high-level flow diagram of another example process 1200 for coupling activation of the sensor device with use of authorized products that can be performed by sensor device 106. Repetitive description of like elements employed in respective embodiments is omitted for sake of brevity.

At 1202, a sensor device comprising or operatively coupled to a processor can receive (e.g., via communication component 904) or capture (e.g., via code capture component 916) an activation code associated with printing on an absorbent article or packaging of the absorbent article. At 1204, the sensor device can determine whether the activation code is valid (e.g., using validation component 908). If, at 1204, the sensor device determines that the activation code is invalid, then at 1208, the sensor device can prevent activation of one or more functionalities of the system based on a determination that the activation code is invalid (e.g., using activation/deactivation component 906).

However, if at 1204 the sensor device determines that the activation code is valid, then at 1206, the sensor device can activate of one or more functionalities of the sensor device (e.g., using activation/deactivation component 906). At 1210, the sensor device can monitor use of the sensor device in association with a use restriction associated with the activation code (e.g., using use tracking component 914). At 1212 the sensor device can evaluate the tracked use to determine whether the use restriction has been reached (e.g., using use tracking component 914). For example, in an implementation in which the use restriction restricts activation of the one or more functionalities based on use of the sensor device with a maximum number of different absorbent articles, the sensor device can determine whether the sensor device has been used with (e.g., reattached to) the maximum allotted number of different absorbent articles. If at 1212 the sensor device determines that the use restriction has not been reached, then the sensor device can continue to monitor the use at 1210. However, if at 1212 the sensor device determines that the use restriction has been reached, then at 1214, the sensor device can deactivate the one or more functionalities (e.g., using activation/deactivation component 906).

Figure 13:
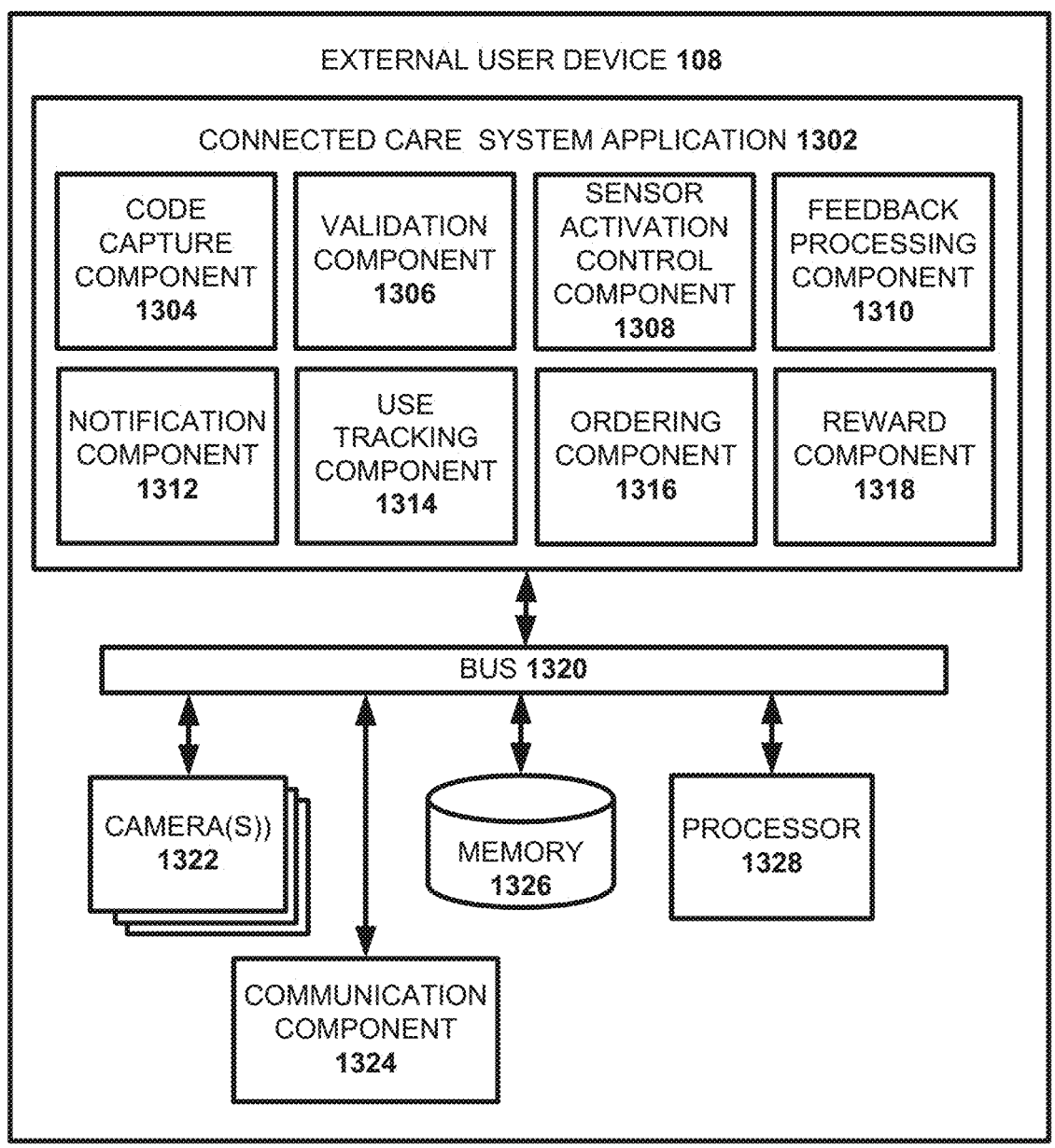
FIG. 13 illustrates a block diagram of an example external user device that facilitates coupling activation of a sensor device with use of authorized products in accordance with one or more embodiments of the disclosed subject matter.

FIG. 13 illustrates a block diagram of an example external user device (e.g., external user device 108) that facilitates coupling activation of a sensor device with use of authorized products. In the embodiment shown, the external user device 108 can include various computer executable components associated with a connected care system application 1302 executed by the external user device 108. For example, the connected care system application 1302 can include a dedicated client application, a web-application, a thin client application, a hybrid application, or the like. For example, in some embodiments, the connected care system application 1302 can be configured to provide various features and functionalities associated with use of the sensor device 106 in association with communication with at least one external server device 602 (e.g., a cloud-based server device, an application server, and the like).

The external user device 108 can further include one or more cameras 1322, a communication component 1324, at least one memory 1326, at least one processor 1328, and a device bus 1320. In various embodiments, the at least one memory 1326 can be configured to store computer executable components and instructions (e.g., the connected care system application 1302 and/or one or more components of the connected care system application 1302). The at least one processor 1328 can facilitate operation of the computer executable components and instructions stored in the at least one memory 1326. The device bus 1320 can couple the various components of the external user device 108, including, but not limited to, the connected care system application 1302, the one or more camera 1322, the communication component 1324, the memory 1326 and the processor 1328.

In the embodiment shown, the connected care system application 1302 can include a code capture component 1304, a validation component 1306, a sensor activation control component 1308, a feedback processing component 1310, a notification component 1312, a use tracking component 1314, an ordering component 1316, and a reward component 1318.

In various embodiments, the code capture component 1304 can include same or similar features and functionalities as code capture component 916. For example, the code capture component 1304 can be configured to activate the one or more cameras 1322 of the external user device 108 to capture and/or extract an activation and/or identification code (e.g., QR code 304 or the like) as printed on or within an absorbent article and/or packaging of the absorbent article. In another example, the code capture component 1316 can activate an RFID reader of the external user device 108 to facilitate capturing an activation code and/or an identification code provided on or within an absorbent article and/or absorbent article packaging in the form of an RFID tag.

In various embodiments, the validation component 1306 can facilitate performing a code validation process in association with capture and/or receipt of an identification code by the code capture component 1304. For example, in some embodiments, the validation component 1306 can send the identification code to the external server device 602 for validation in association with a validation request. The validation component 1306 can further receive an activation code from the external server device 602 based on a determination that the identification code is valid.

In some embodiments, the sensor activation control component 1308 can facilitate sending an activation code to the sensor device 106 for activating the one or more functionalities. For example, in some embodiments, the sensor activation control component 1308 can automatically send the activation code to the sensor device 106 for activating the sensor device 106 when the sensor device is within wireless communication range of the external user device 108. Additionally, or alternatively, the sensor activation control component 1308 can send the activation code to the sensor device in association with a request, issued via user interaction with the connected care system application 1302, to activate the one or more functionalities using the activation code. In some embodiments, the sensor activation control component 1308 can further determine and/or provide activated use restrictions with activation codes in association with sending the activation code to the sensor device 106. For example, in some implementations, the sensor activation control component 1308 can determine a use restriction associated with a particular activation code (e.g., regarding the duration of time the sensor device is authorized to remain activated, regarding the number of absorbent articles with which the activated sensor device can be used with before requiring reactivation using a new code, and the like). The sensor activation control component 1308 can further including information identifying the use restrictions with the activation code in association with sending the activation code to the sensor device.

In various embodiments, the feedback processing component 1310, the notification component 1312, the use tracking component 1314 and the communication component 1324 can include same or similar features and functionalities as that described with the corresponding components shown in FIG. 9 (e.g., the feedback processing component 910, the notification component 912, the use tracking component 914, and the communication component 904, respectively. In addition, the communication component 1324 can include same or similar features and functionalities as communication component 904. Repetitive description of like elements employed in respective embodiments is omitted for sake of brevity.

The feedback processing component 1310 may determine sensory feedback information based on received sensor data provided by the sensor device 106. Additionally, or alternatively, the feedback processing component 1310 of the external user device can receive additional inputs, such as but not limited to: information regarding sensor device, the time the absorbent article was attached to a wearer, time the sensor device was attached to the absorbent article, the current time, wearer information (e.g., demographic information such as sex, age, weight of wearer, biometric information of the wearer, whether the wearer is toilet training, degree of wearer incontinence), temperature, humidity, caregiver preference information and/or ambient sensor information. The feedback processing component 1310 may use these additional inputs separately and/or in combination with the information received from the sensor device.

With these embodiments, the feedback processing component 1310 can determine a status of the absorbent article based at least in part upon the sensor data received from the sensor device 106 and contextual information (e.g., wear time of the absorbent article and wearer demographic information). Contextual information, for example, can be input by consumers, retrieved via other sensors or information sources (e.g., thermostats). In a non-limiting example, the feedback processing component can use a property change detected in an indicator 112 and wear time. Wear time, for example, may be described as the time determined between attachments of two fresh absorbent articles. In various implementations, the feedback processing component 1310 can determine and/or infer exudate fullness using one or more of the following functions: (Urine Fullness=f(Property Change Detection, wear time, wearer data and other data)); and Property Change Detection=f(color sensor data).

The notification component 1312 can further report an exudate content quantity, for example, to a user to indicate a percent or other indication of absorbent article fullness or remaining capacity on the sensor device 102 for displaying at the external user device 108. In some nonlimiting examples, the external user device 108 can display a graphical or numerical representation of exudate content quantity or remaining capacity of the absorbent article.

In the embodiment shown, the connected care system application can also include an ordering component 1316 and a reward component 1318. In some embodiments, as described with reference to use tracking component 914, the use tracking component 1314 can similarly track an amount of the absorbent articles used with the sensor device 106 (e.g., based in part on frequency of activation, use associated with activation, number of detachment/reattachment events, number of wetness events detected etc.). In some embodiments, the ordering component 1316 can facilitate ordering additional absorbent authorized for use with the sensor device 106 based on the tracked use. For example, the ordering component 1316 can determine based on previous order and an amount of product used when the user will be needed additional product (e.g., when the user is running low). The ordering component 1316 can further facilitate automatically ordering the additional product based on the tracked use. In some embodiments, the ordering component 1316 and/or the reward component 1318 can further associate an activation code for the sensor device 106 with the entity account based on confirmation that the order for the additional produce was made. The reward component 1318 can further be configured to issues a reward to an entity account associated with the sensor device 106 and/or external user device 108 based on at least one of, the activation of the sensor device 106 and/or or receipt of confirmation that the order was made and/or receipt of authorization for ordering of the additional absorbent articles.

Additionally, or alternatively, the reward component 1318 can provide the external device 108 and/or a user account associated with the external device 108 and/or the sensor device 106 with an activation code and/or other rewards based on various other types of user activity associated with use of the connected care system/application. For example, such other user activity can include using interactive and/or social media features associated with the application, providing manual input regarding behavior of the wearer, wearer habits (e.g., feeding habits, moods, etc.), appearance of the wearer, and other relevant data about the wearer. The reward component can also provide the user account with rewards for activating the sensor device in accordance with the activation protocols implemented by the connected care system (e.g., a user can be rewarded for activating the sensor device using the correct activation mechanism as opposed to using an unauthorized means to activate the sensor device). In some embodiments, the reward component 1318 can also provide the user/user account with rewards for allowing the system to access tracked data about the wearer provided by the sensor device, and other data received and/or generated via the use of the connected care application. Rewards may include a coupon, a discount, a credit, reward points, free shipping, extended activation times for the sensor device, activation of additional features of the connected care application and/or sensor device, ancillary services, products and combinations thereof.

Activation of one or more features of sensor device and/or of the connected care system application 1302 itself can be based on receipt and/or validation of the activation code. For example, in some implementations, the connected care system application 1302 can be configured to only activate one or more features and functionalities of the feedback processing component 1310, the notification component 312, the use tracking component 1314, the ordering component 1316 and/or the reward component 1318, based on receipt and/or validation of the activation code by the external user device 108. In one or more non-limiting examples, the feedback processing component 1310 can be prevented from being able to process sensory feedback received from the sensor device 106 unless the connected care system application 1302 receives a valid activation code. In another implementation, the communication component 1324 can be configured to restrict communication between the sensor device 106 and the external user device 108 based on receipt and/or validation of the activation code by the external user device 108. For example, the communication component 1324 can prevent receipt of sensory feedback data transmitted by the sensor device 106 unless the connected care application receives and/or validates an activation code.

Figure 14:
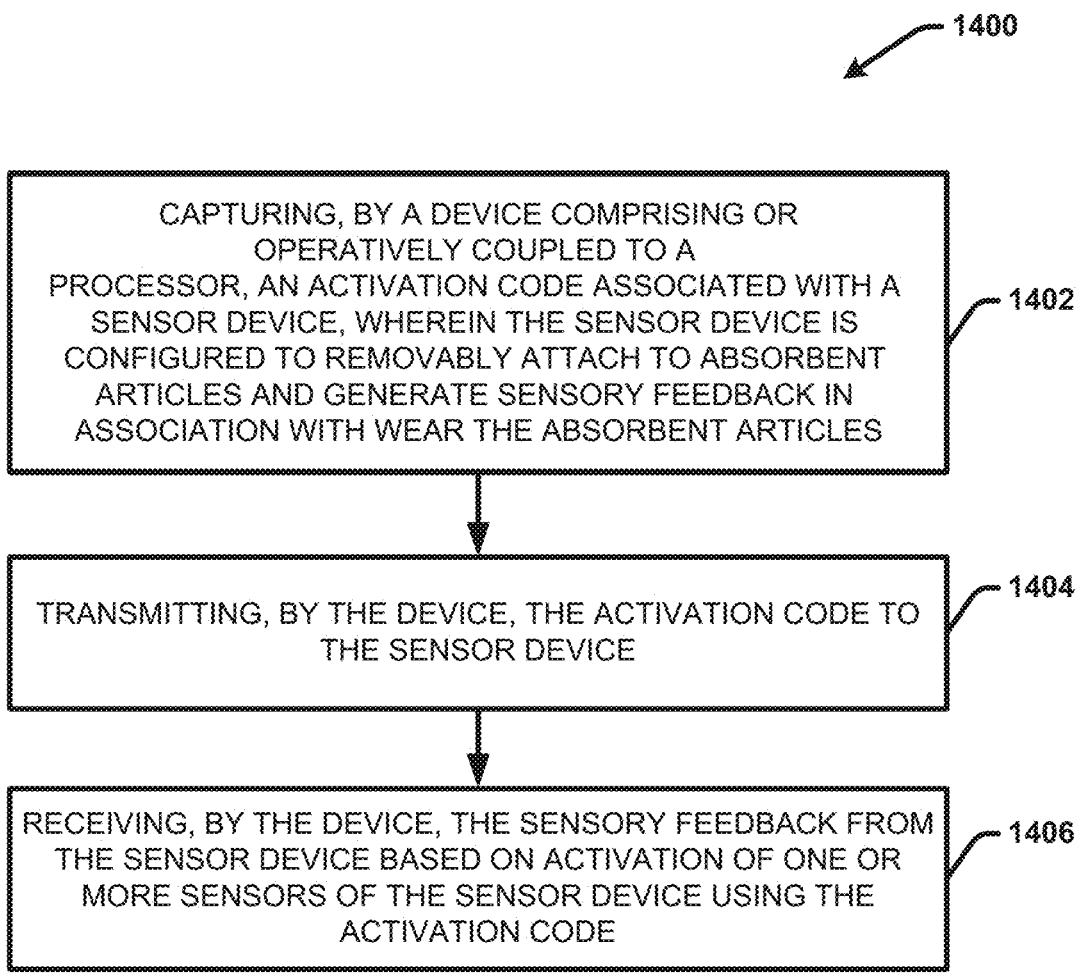
FIG. 14 presents a high-level flow diagram of another example process for coupling activation of a sensor device with use of authorized products in accordance with one or more embodiments of the disclosed subject matter.

FIG. 14 presents a high-level flow diagram of another example process 1400 for coupling activation of a sensor device with use of authorized products. In various embodiments, process 1400 can also be performed by an external user device 108. Repetitive description of like elements employed in respective embodiments is omitted for sake of brevity.

At 1402, a device comprising or operatively coupled to a processor (e.g., external user device 108) can capture (e.g., using code capture component 1304) an activation code associated with a sensor device, wherein the sensor device is configured to removably attach to absorbent articles and generate sensory feedback in association with wear of the absorbent articles. At 1404, the device can transmit the activation code to the sensor device (e.g., using communication component 1324). At 1406, the device can receive (e.g., via the communication component 1304) the sensory feedback from the sensor device based on activation of one or more sensors of the sensor device using the activation code.

Figure 15:
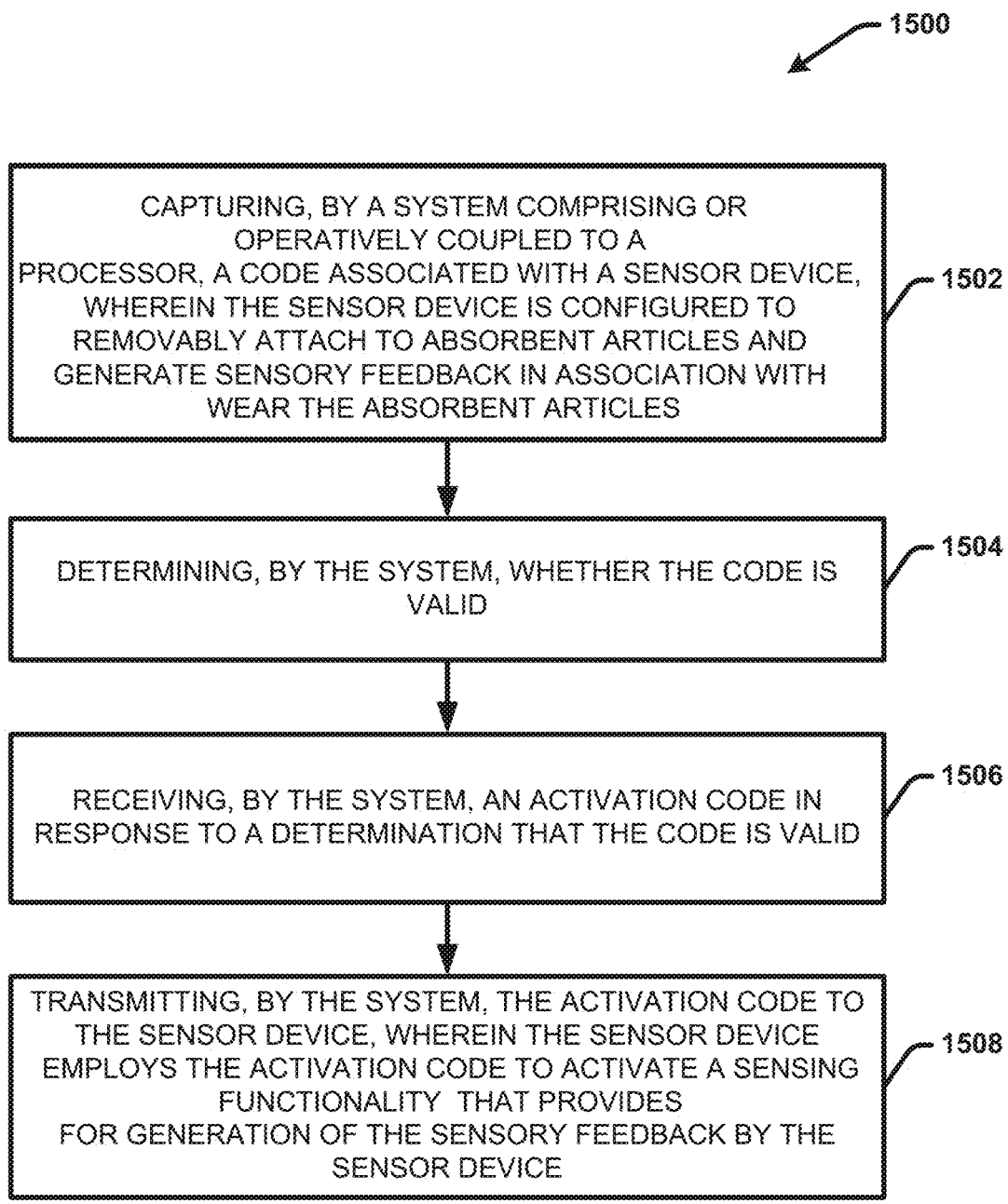
FIG. 15 presents a high-level flow diagram of another example process for coupling activation of a sensor device with use of authorized products in accordance with one or more embodiments of the disclosed subject matter.

FIG. 15 presents a high-level flow diagram of another example process 1500 for coupling activation of a sensor device with use of authorized products that can be performed by the external user device 108. Repetitive description of like elements employed in respective embodiments is omitted for sake of brevity.

At 1502, a system comprising or operatively coupled to a processor (e.g., system 600), can capture (e.g., using code capture component 1304) a code associated with a sensor device 106, wherein the sensor device is configured to removably attach to absorbent articles and generate sensory feedback in association with wear of the absorbent articles. For example, the activation code can be or be embodied within a visual identifier (e.g., a QR code) printed on or within one or more of the absorbent articles and/or packaging of the absorbent articles. At 1504, the system can determine whether the activation code is valid (e.g., using validation component 1306). At 1506, the system can receive an activation code in response to a determination that the code is valid (e.g., via communication component 1324). At 1508, the system can transmit the activation code to the sensor device (e.g., via communication component 1324), wherein the sensor device employs the activation code to activate a sensing functionality of the sensor device that provides for generation of the sensory feedback by the sensor device.

Figure 16:
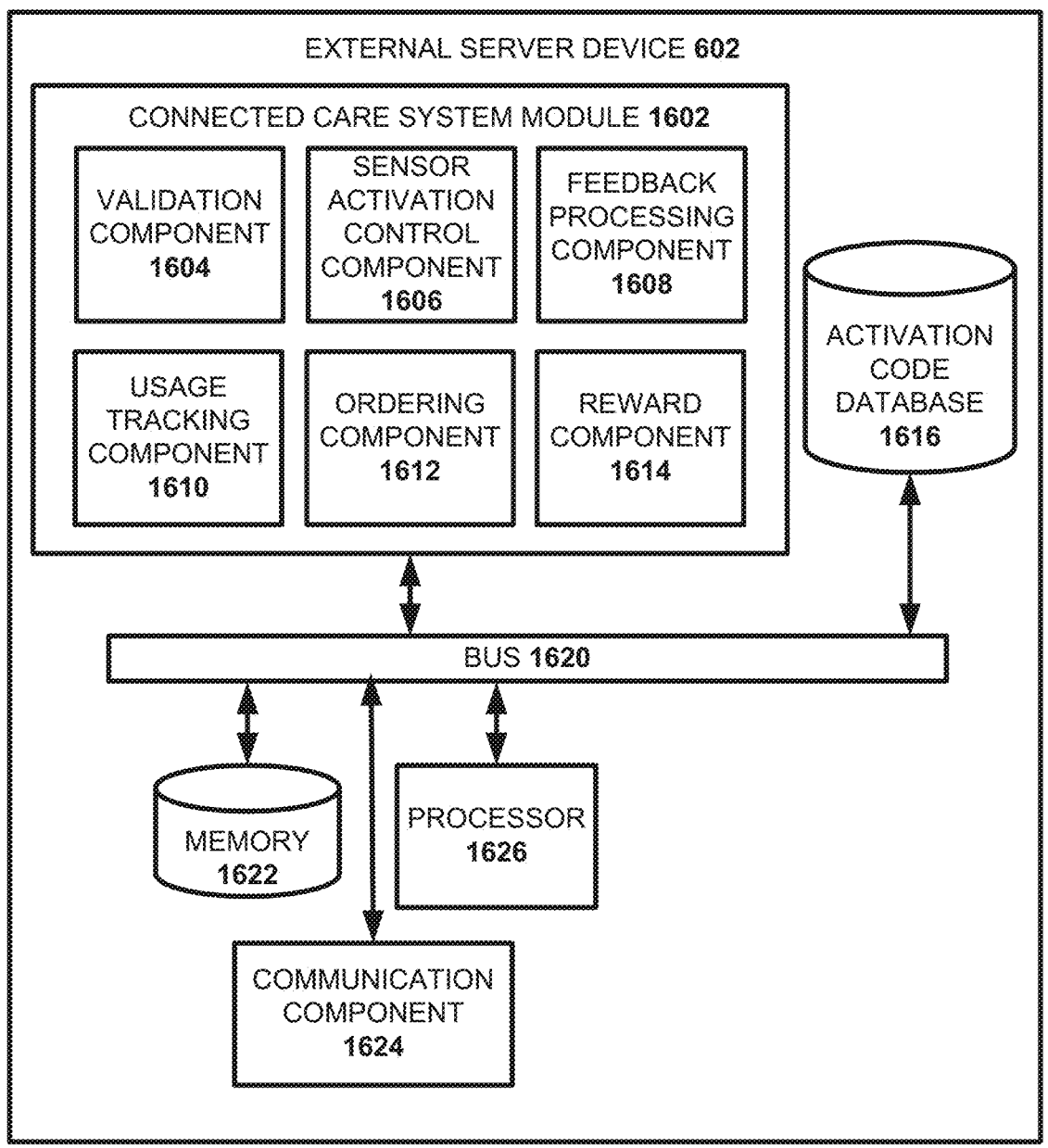
FIG. 16 illustrates a block diagram of an example external server device that facilitates coupling activation of a sensor device with use of authorized products in accordance with one or more embodiments of the disclosed subject matter.

FIG. 16 illustrates a block diagram of an example external server device (e.g., server device 602) that facilitates coupling activation of a sensor device with use of authorized products. In the embodiment shown, the external server device 602 can include various computer executable components associated with a connected care system module 1602 executed by the external server device 1602. For example, the connected care system module 1602 can include same or similar components as the connected care system application 1302. For example, the connected care system module 1602 can include a validation component 1604, a sensor activation control component 1606, a feedback processing component 1608, a use tracking component 1610, an ordering component 1612 and a reward component 1614. In various embodiments, these components of the connected care system module 1602 can provide same or similar features and functionalities as the corresponding component associated with the connected care system application 1302. Repetitive description of like elements employed in respective embodiments is omitted for sake of brevity.

In some embodiments, the validation component 1604 can be configured to validate an identification code received from an external user device 108 and in turn provide the external user device 108 with an activation code. In some embodiments, the external server device 602 can include an activation code database 1616 that maintains information identifying valid, invalid and/or expired identification codes. The validation component 1604 can further determine whether an identification code is valid, invalid or expired based on looking up the identification code in the activation code database 1616. In some implementations, the activation code database 1616 can further association unique activation codes with each corresponding identification code.

In addition to the connected care system module 1602, the external server device 602 can include a communication component 1624, at least one memory 1622, at least one processor 1626, and a device bus 1620. The communication component 1624 can include same or similar features and functionalities as communication component 904. In various embodiments, the at least one memory 1622 can be configured to store computer executable components and instructions (e.g., the connected care system module 1602 and/or one or more components of the connected care system module 1602). The external server device 602 can also include at least one processor 1328 to facilitate operation of the computer executable components and instructions by external server device 602.

Figure 17:
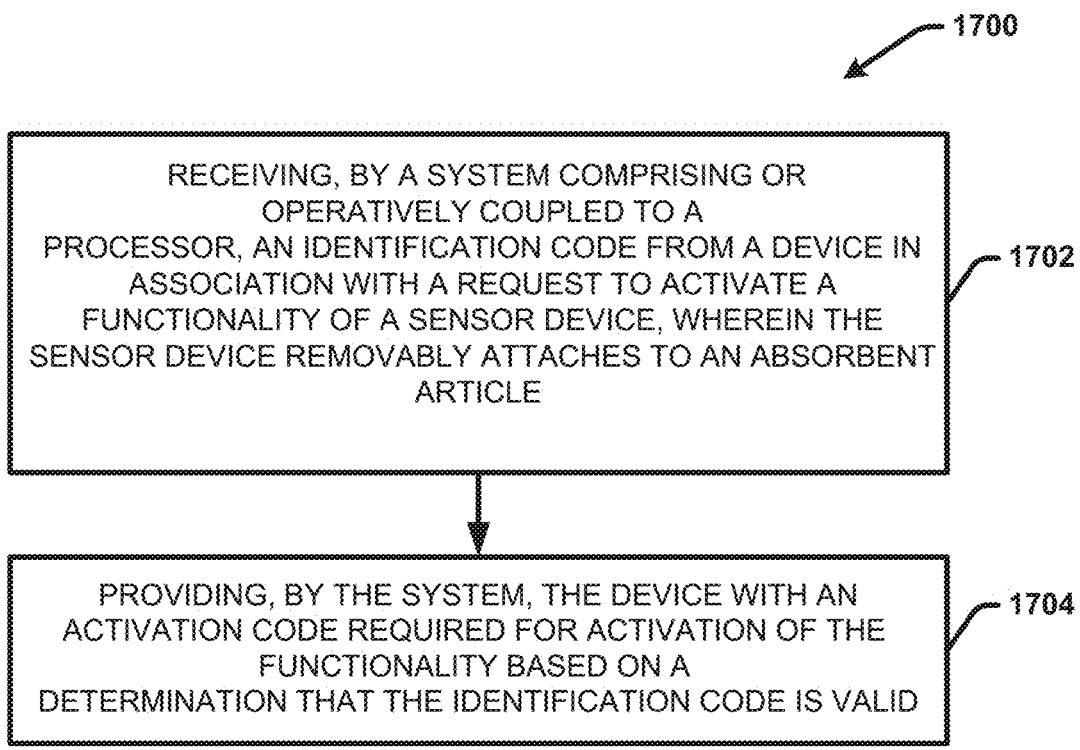
FIG. 17 presents a high-level flow diagram of another example process for coupling activation of a sensor device with use of authorized products in accordance with one or more embodiments of the disclosed subject matter.

FIG. 17 presents a high-level flow diagram of another example process 1700 for coupling activation of a sensor device with use of authorized products. In various embodiments, process 1700 can be performed by the external server device 602. Repetitive description of like elements employed in respective embodiments is omitted for sake of brevity. At 1702, a system comprising or operatively coupled to a processor (e.g., system 600), can receive (e.g., via communication component 1624) an identification code from a device (e.g., external user device 108) in association with a request to activate a functionality of a sensor device 106, wherein the sensor device removably attaches to an absorbent article 102. At 1704, the system can provide the device with an activation code required for activation of the functionality of the system based on a determination that the identification code is valid (e.g., via validation component 1604).

Figure 18:
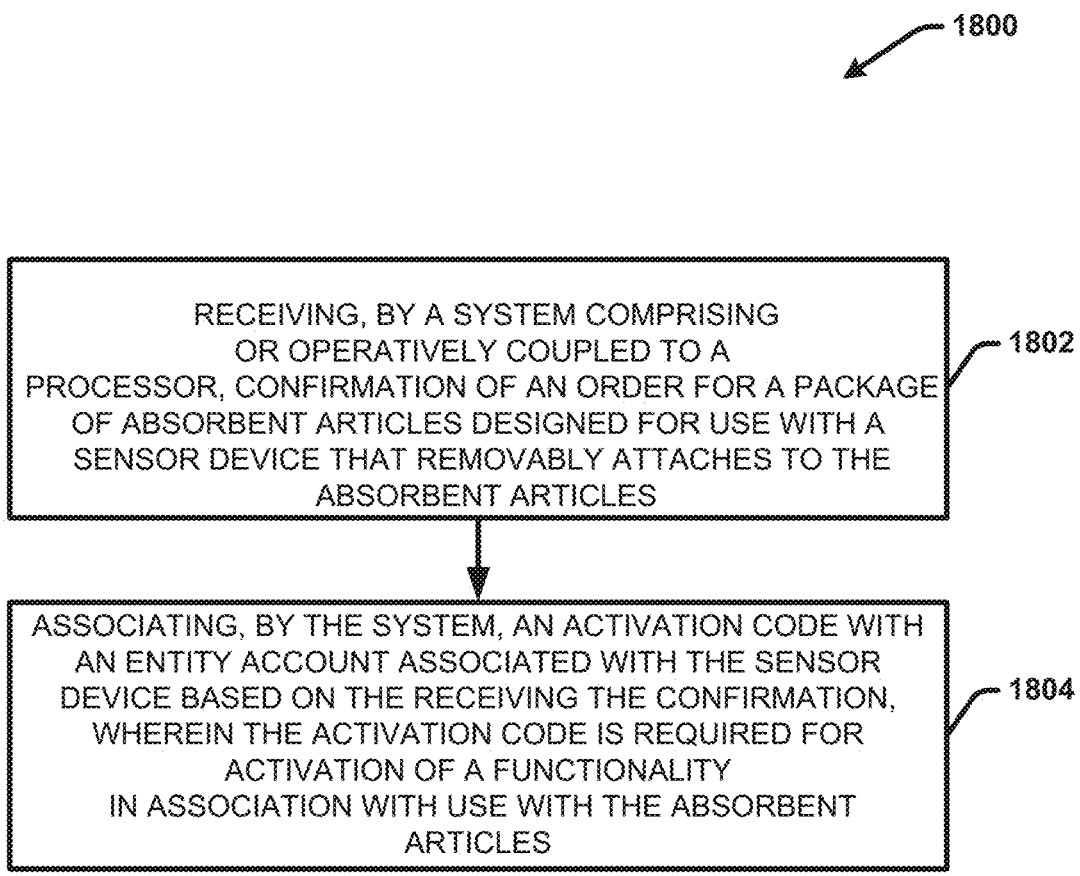
FIG. 18 presents a high-level flow diagram of another example process for coupling activation of a sensor device with use of authorized products in accordance with one or more embodiments of the disclosed subject matter.

FIG. 18 presents a high-level flow diagram of another example process 1800 for coupling activation of a sensor device with use of authorized products that can be performed by an external sever device 602. Repetitive description of like elements employed in respective embodiments is omitted for sake of brevity. At 1802, a system comprising or operatively coupled to a processor (e.g., system 600), can receive confirmation of an order (e.g., via ordering component 1612) for a package of absorbent articles designed for use with a sensor device 106 that removably attaches to the absorbent articles. At 1804, the system can associate an activation code with an entity account associated with the sensor device based on the receipt of the confirmation (e.g., via sensor activation control component 1606 and/or reward component 1614), wherein the activation code is required for activation of a functionality of the system in association with use with the absorbent articles.

While the figures depict activation codes being received by the sensor device, it is also contemplated that the activation code may be received by an external user device or external server device, cloud-based system, or the like to activate and/or restrict one or more functionalities of the system. For instance, the external user device may scan the activation code as described above and an application on the external user device may be activated. Additionally, or alternatively, the activation code may activate a process in the external server device.

The flowcharts and block diagrams in the Figures illustrate the architecture, functionality, and operation of possible implementations of systems, methods, and computer program products according to various embodiments of the present invention. The functions noted in the blocks can occur in the order shown in the Figures or out of the order noted in the Figures, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, handheld computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system comprising
   a sensor device, comprising:
      a housing that attaches to an absorbent article configured to absorb and contain bodily exudates, the absorbent article comprising a secret code; and
      at least one sensor formed on or within the housing configured to capture sensor data in association with wear of the absorbent article; and
   a processor that executes computer executable components;
   wherein the computer executable components comprise:
      a communication component that receives an activation code;
      a validation component that validates the activation code based at least in part on the secret code; and
      an activation component that activates a functionality based on validation of the activation code.

2. The system of claim 1, wherein the sensor device comprises the processor.

3. The system of claim 2, wherein the communication component receives the activation code from a device external to the sensor device.

4. The system of claim 1, wherein an external server device, a cloud-based system, an edge-based system or an external device comprises the processor.

5. The system of claim 1, wherein the activation code is absent from a package that contained the absorbent article, provided on the interior surface of the package, and/or provided on or within the absorbent article.

6. The system of claim 1, wherein the functionality comprises operation of one of the group consisting of: one or more sensors of the sensor device; the processor; storing logic that provides for storing captured and/or processed sensor data in a memory, a communication protocol that provides for transmitting the captured and/or processed sensor data to an external user device, an external server device, a cloud-based system, an edge-based system and/or a software application; the software application; one or more computer executable components; a restriction protocol to restrict any of the foregoing functionalities to use of the sensor device with one or more absorbent articles made by a same manufacturer of the absorbent article and combinations thereof.

7. The system of claim 6, wherein the functionality comprises at least one of: the capture of the sensor data via the at least one sensor, processing of the sensor data, or communication of the sensor data to a device external to the sensor by the communication component.

8. The system of claim 1, wherein the computer executable components further comprise:
   a feedback processing component configured to monitor and process the sensor data to generate feedback information regarding at least one of: usage of the absorbent article or activity of a wearer of the absorbent article; and wherein the functionality comprises monitoring and processing of the sensor data by the feedback processing component.

9. The system of claim 1, wherein the communication component receives the activation code based on a determination that activation code is associated with an entity account associated with the sensor device.

10. The system of claim 1, wherein the sensor device is configured to removably attach to and be reused with a plurality of absorbent articles, and wherein the activation component restricts the activation of the functionality based on use of the sensor device with a defined number of absorbent articles before the functionality of the sensor device requires reactivation.

11. The system of claim 1, wherein the sensor device is configured to removably attach to and be reused with a plurality of absorbent articles, and wherein the activation component restricts the activation of the functionality for a defined amount of time before the functionality requires reactivation.

12. A system comprising:
   a sensor device configured to removably attach to an absorbent article and generate sensor data in association with wear of the absorbent article, wherein the absorbent article comprises a secret code capable of being detected by the sensor device;
   a processor that executes computer executable components; wherein the computer executable components comprise:
      a code capture component that captures an activation code associated with a device external to the sensor device;
      a validation component that performs a code validation process to determine whether the code is valid based on a combination of the secret code and the activation code; and
      an activation component that activates a functionality based on a determination that the code is valid.

13. The system of claim 12, wherein the functionality comprises a sensing functionality of the sensor device that provides for generation of the sensor data by the sensor device.

14. The system of claim 12, wherein the activation code comprises a visual code or symbol printed on an interior surface of a package that contained one or more of the absorbent articles.

15. The system device of claim 12, wherein the activation code comprises a visual code or symbol printed on one or more of the absorbent articles.

16. The system of claim 12, wherein the activation component restricts the functionality based on use of the sensor device with only absorbent articles produced by a same manufacturer as the absorbent articles.

17. The system of claim 16, wherein computer executable components further comprise:
   a use tracking component that tracks an amount of the absorbent articles used with the sensor device based in part on the activation; and
   an ordering component that orders the additional absorbent articles from the same manufacturer based on the amount.

18. The system of claim 12, wherein the computer executable components further comprise:
   a reward component that issues a reward to an entity account associated with the sensor device based on the activation, receipt of an order for additional absorbent articles, and/or receipt of authorization for ordering of the additional absorbent articles.

19. A method comprising:
   receiving, by a sensor device comprising or operatively coupled to a processor, an activation code from a device external to the sensor device, wherein the sensor device removably attaches to an absorbent article configured to absorb and contain bodily exudates, wherein the absorbent article comprises a secret code;
   validating the activation code based on a combination of the secret code and the activation code; and
   activating, by the sensor device, a restriction protocol to restrict a functionality of the sensor device to use with one or more absorbent articles made by a same manufacturer of the absorbent article of the sensor device based on receipt of the activation code.

20. The method of claim 19, wherein the functionality comprises at least one of: capture of sensor data via one or more sensors of the sensor device, processing of the sensor data, or communication of the sensor data to the device.

21. The method of claim 19, wherein the receiving comprises receiving the activation code from the device in association with capture and verification, by the device, of an identification code provided on or within a package that contained the absorbent article.

* * * * *